United States Patent [19]

Nakada et al.

[11] Patent Number: 5,301,061
[45] Date of Patent: Apr. 5, 1994

[54] ENDOSCOPE SYSTEM

[75] Inventors: Akio Nakada, Lake Success; Peter G. Lorenz, Massapequa, both of N.Y.; Minoru Okada, Sagamihara, Japan; Nobuyuki Sakamoto, Hachioji, Japan; Yoshikazu Tohjoh, Fussa, Japan; Katsunori Sakiyama, Hachioji, Japan

[73] Assignee: Olympus Optical Co., Ltd., Tokyo, Japan

[21] Appl. No.: 489,573

[22] Filed: Mar. 7, 1990

[30] Foreign Application Priority Data

Jul. 27, 1989 [JP] Japan .................. 1-196350
Jan. 31, 1990 [JP] Japan .................. 2-23546

[51] Int. Cl.⁵ .................. G03B 11/04; A61B 1/00; H04N 7/18
[52] U.S. Cl. .................. 359/362; 359/511; 128/4; 348/75
[58] Field of Search .................. 350/96.26, 574; 356/241, 383–385; 128/4–7, 395; 606/14, 18, 19; 359/882, 574, 226, 362–363, 503–512, 896; 358/98

[56] References Cited

U.S. PATENT DOCUMENTS

| | | | |
|---|---|---|---|
| 4,319,563 | 3/1982 | Kubota | 128/6 |
| 4,558,691 | 12/1985 | Okada | 128/6 |
| 4,640,124 | 2/1987 | Diener et al. | 73/116 |
| 4,646,722 | 3/1987 | Silverstein et al. | 128/4 |
| 4,648,399 | 3/1987 | Nakada | 606/46 |
| 4,659,195 | 4/1987 | D'Amelio et al. | 350/574 |
| 4,660,982 | 4/1987 | Okada | 356/383 |
| 4,696,544 | 9/1987 | Costella | 350/96.26 |
| 4,721,097 | 1/1988 | D'Amelio | 128/4 |
| 4,726,355 | 2/1988 | Okada | 128/4 |
| 4,742,817 | 5/1988 | Kawashima et al. | 128/4 |
| 4,763,662 | 8/1988 | Yokoi | 128/4 |
| 4,770,188 | 9/1988 | Chikama | 128/772 |
| 4,779,130 | 10/1988 | Yabe | 128/4 |
| 4,784,117 | 11/1988 | Miyazaki | 128/4 |
| 4,784,463 | 11/1988 | Miyazaki | 350/96.26 |
| 4,825,259 | 4/1989 | Berry, Jr. | 356/383 |
| 4,852,551 | 8/1989 | Opie et al. | 128/4 |
| 4,857,057 | 8/1989 | Sanagi | 128/4 |
| 4,878,485 | 11/1989 | Adair | 128/6 |
| 4,889,106 | 12/1989 | Watanabe | 128/4 |
| 4,895,138 | 1/1990 | Yabe | 128/6 |
| 4,920,961 | 5/1990 | Grossi et al. | 606/14 |
| 4,947,827 | 8/1990 | Opie et al. | 128/4 |
| 4,951,677 | 8/1990 | Crowley et al. | 128/4 |

FOREIGN PATENT DOCUMENTS 48-31672 9/1973 Japan .
57-37322 3/1982 Japan .
58-77316 5/1983 Japan .
61-149118 7/1986 Japan .
62-102731 5/1987 Japan .
63-260524 10/1988 Japan .

Primary Examiner—Bruce Y. Arnold
Assistant Examiner—Thong Nguyen
Attorney, Agent, or Firm—Armstrong, Westerman, Hattori, McLeland, & Naughton

[57] ABSTRACT

The endoscope system of this invention is formed of an endoscope having an insertable part provided in the tip part with an illuminating window and a receiving window receiving an object image illuminated by an illuminating light emitted from the illuminating window and a plurality of sheaths selectively and removably connected to the endoscope, inserted through the insertable part when connected to the endoscope and having respectively different functions.

15 Claims, 31 Drawing Sheets

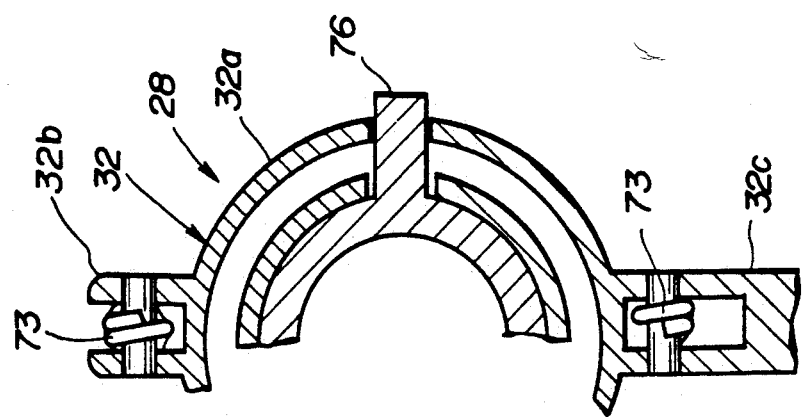
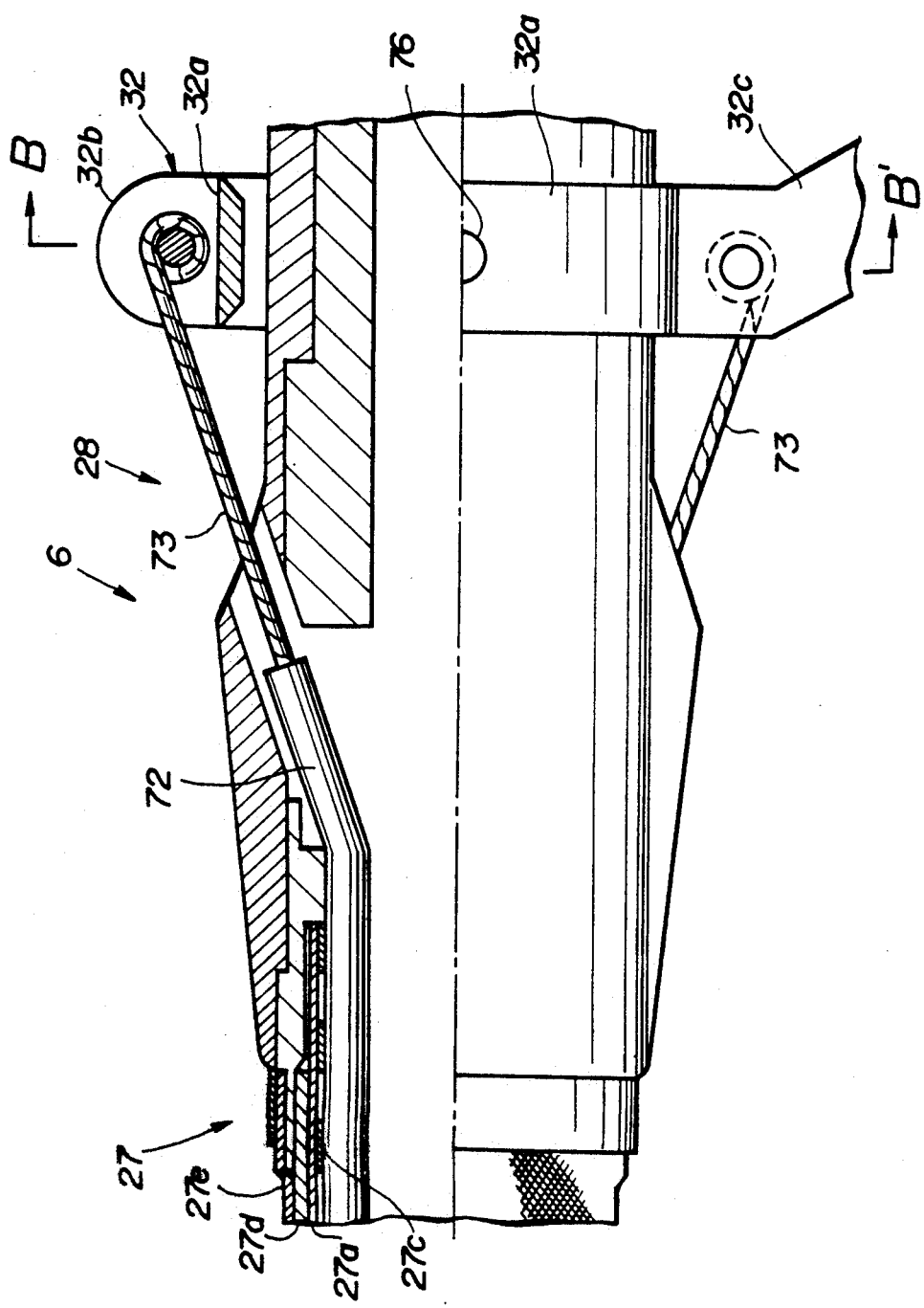

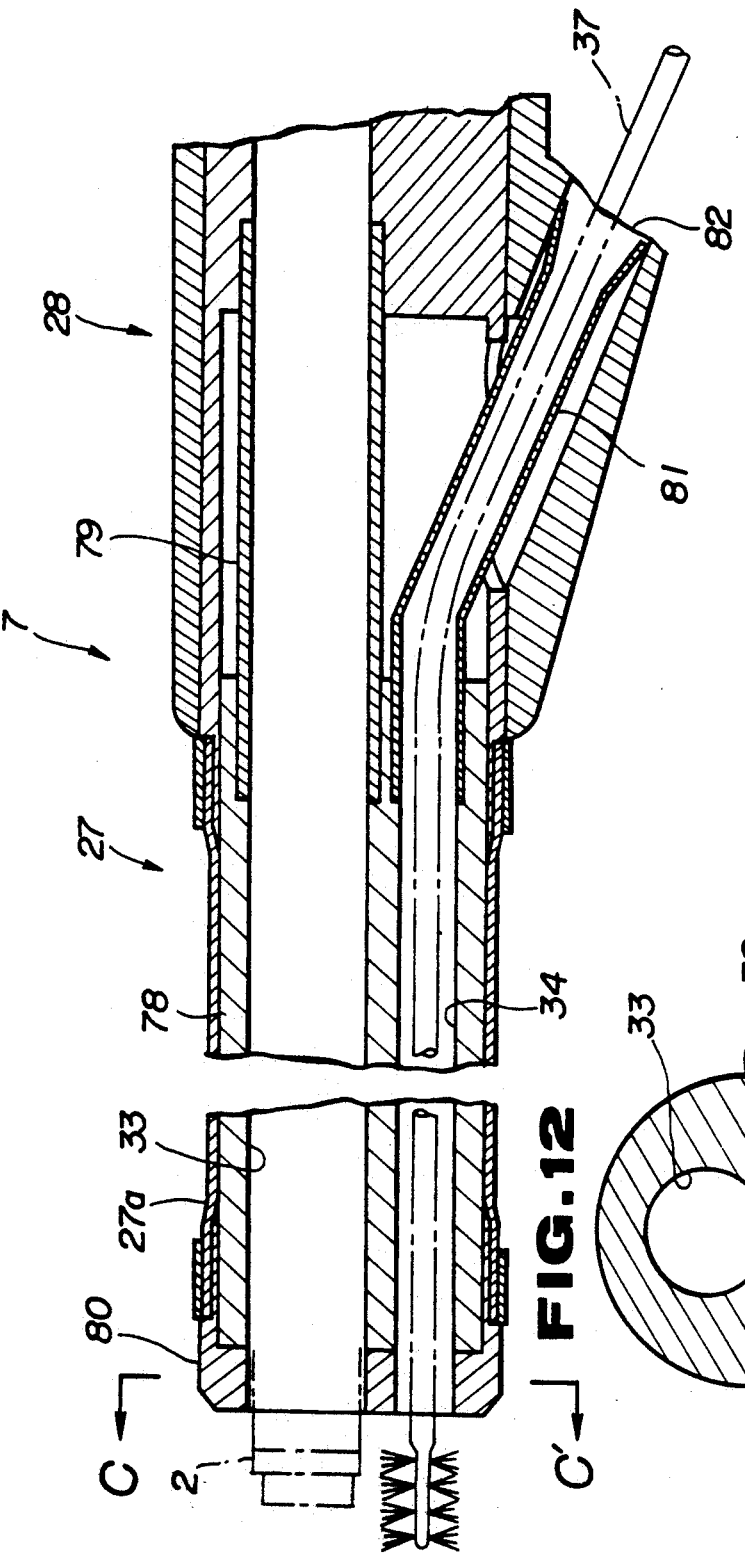

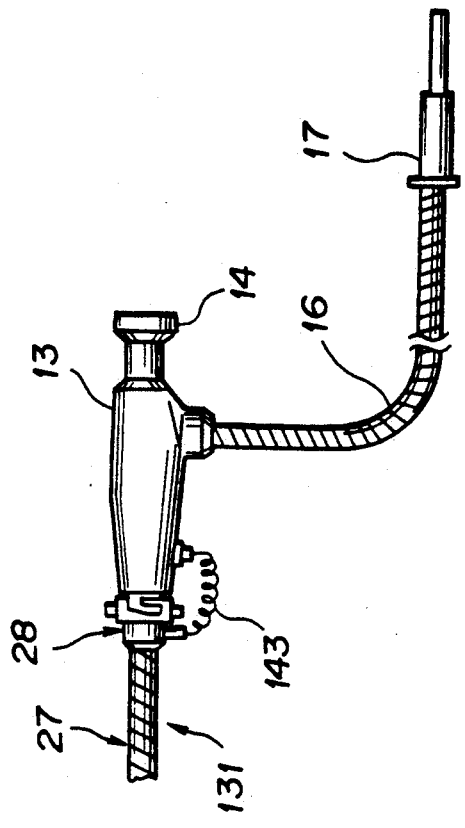
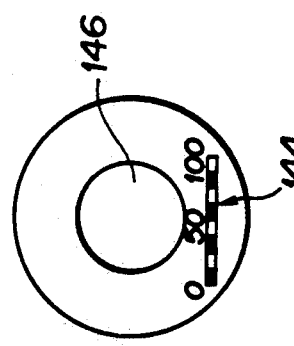
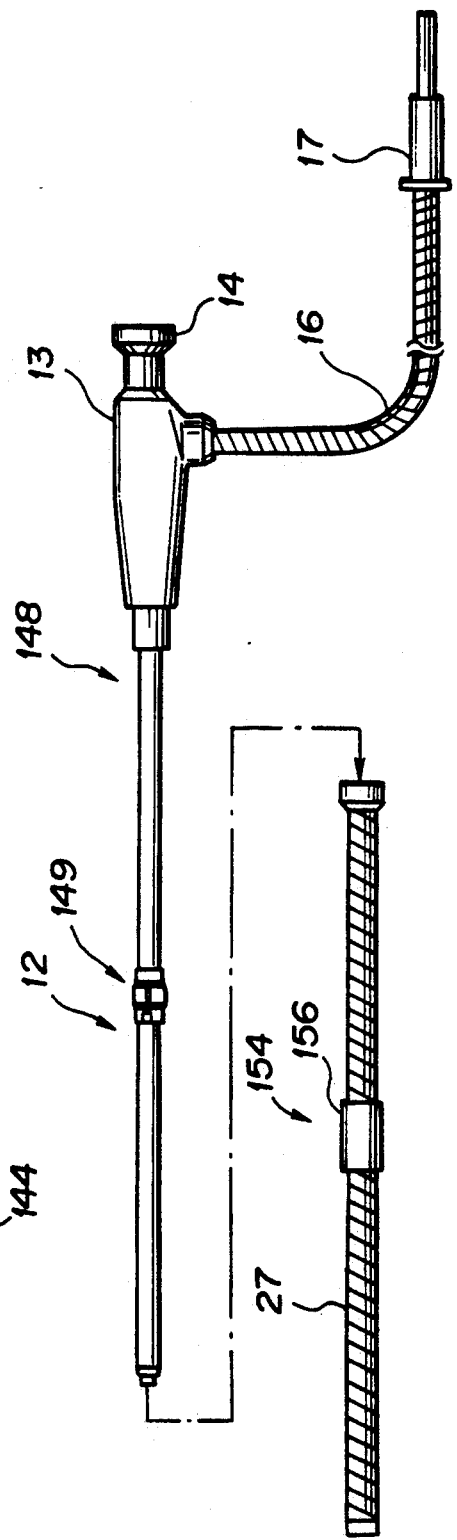
FIG. 27
FIG. 28
FIG. 29

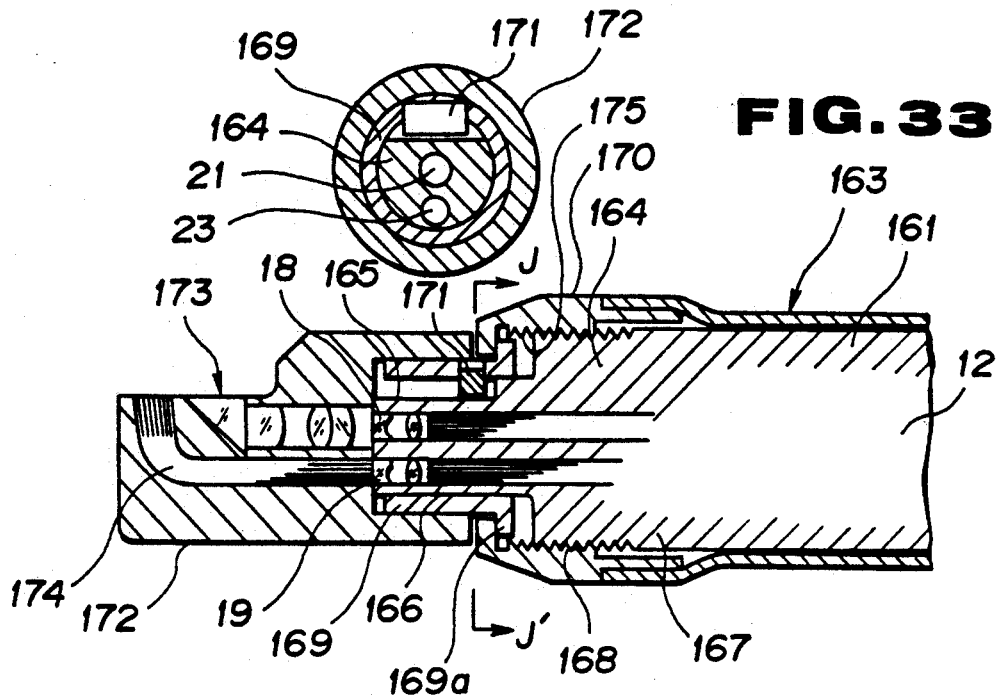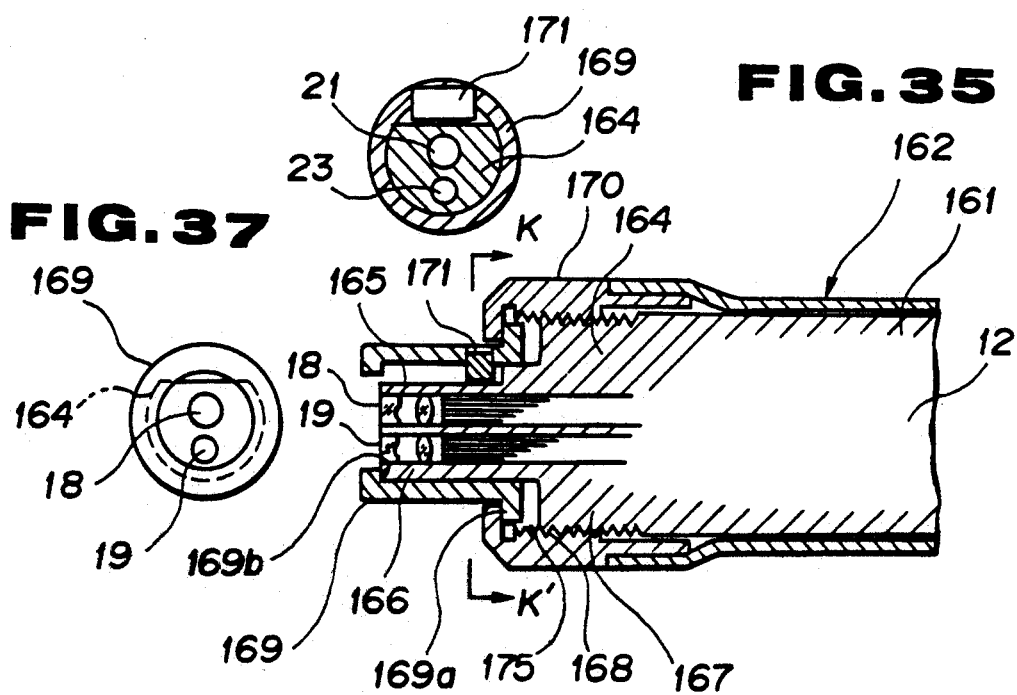

FIG. 47
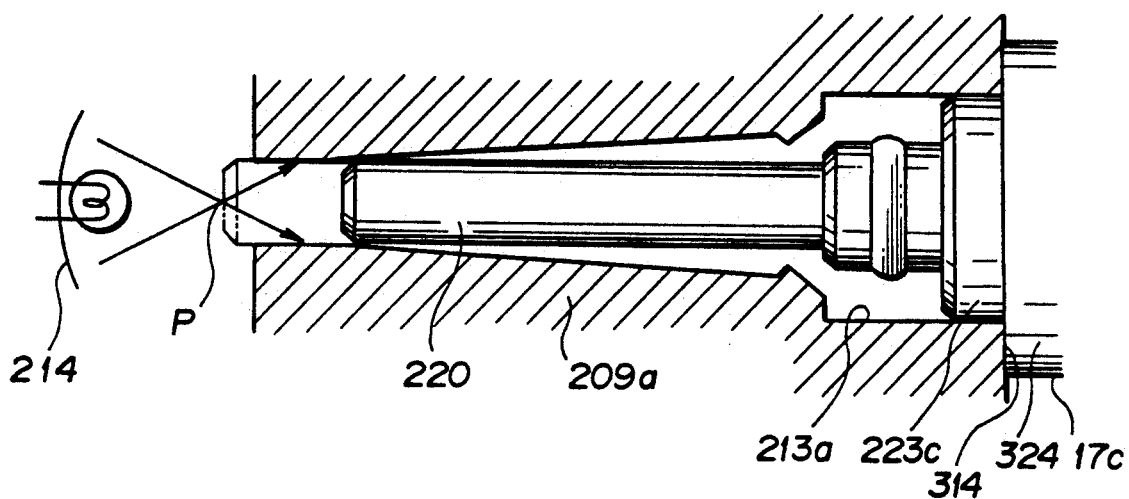
FIG. 45(A) FIG. 45(B)
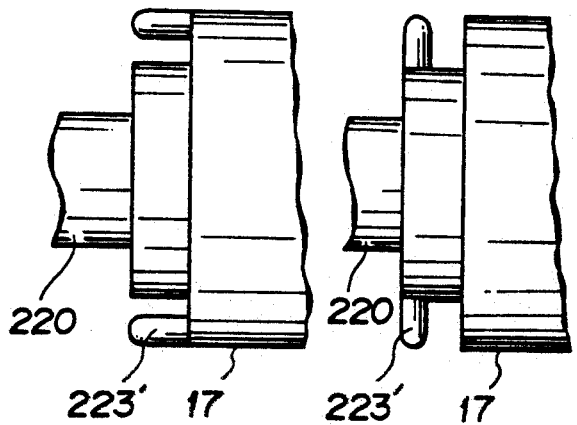
FIG. 48
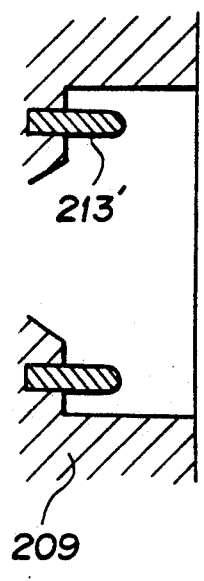

FIG. 52(A)
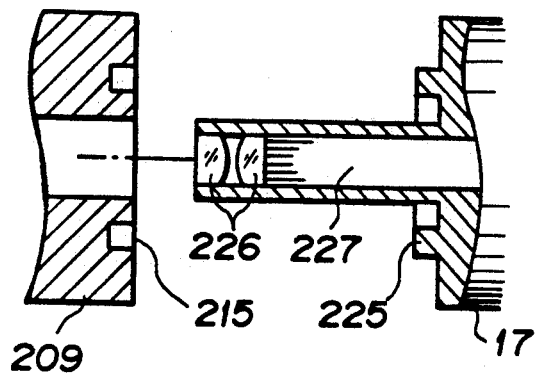
FIG. 52(B)   FIG. 52(C)
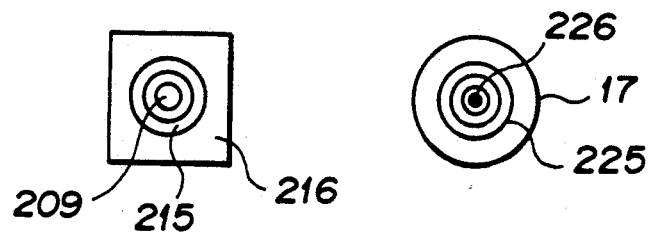
FIG. 53
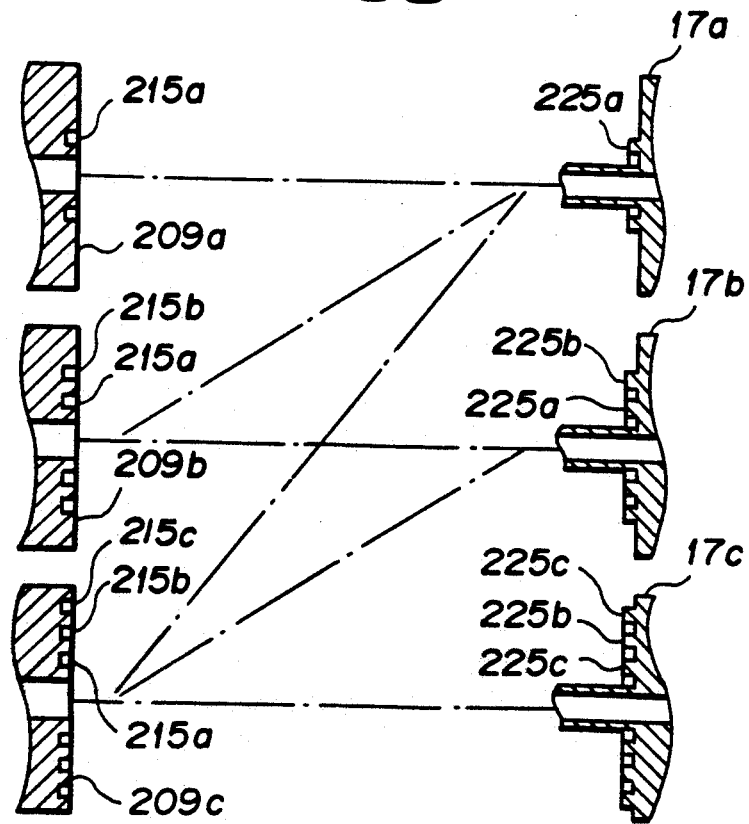

ENDOSCOPE SYSTEM

FIELD AND BACKGROUND OF THE INVENTION

This invention relates to an industrial endoscope system for inspecting the interior of an automobile engine or the like.

Recently, there are extensively used medical endoscopes which can be inserted in an elongate insertable part into a body cavity to observe organs within the body cavity or, as required, through a catheter channel to collect tissues within the living body by using a catheter and diagnose the affected part in detail. In the industrial field, there are also extensively used industrial endoscopes by which the interior of a boiler, turbine, engine or chemical plant can be observed or inspected.

A sheath for internally inserting a light guide bundle of an illuminating means, removably fitted on the outer periphery of the insertable part of the above mentioned endoscope, is disclosed in the publication of Japanese Utility Model Application Publication No. 31672/1973.

An industrial endoscope in which the insertable part is coated with a metal blade to improve the durability is disclosed in the publication of Japanese Patent Application Laid Open No. 37322/1982.

Further, a rigid sheath fitted with a reflecting mirror for converting the visual field is disclosed in the publication of Japanese Patent Application Laid Open No. 149118/1986.

As mentioned above, various sheaths removably fitted on the outer periphery of the endoscope insertable part are known.

However, the removably fitting structure to the endoscope is different in the respective sheaths. Various sheaths different in the removably fitting function can not be used as combined for one endoscope. That is to say, one endoscope can be combined with only one sheath. Therefore, there have been problems that the endoscope is limited in use and, as many endoscopes as there are uses must be prepared, and an economic burden is placed on the user.

OBJECT AND SUMMARY OF THE INVENTION

An object of the present invention is to provide an endoscope system wherein a plurality of sheaths different in the removably fitting function are prepared for one endoscope so that, as required, a selected sheath may be combined with the endoscope for various uses.

The endoscope system of the present invention comprises an endoscope having a flexible insertable part provided in the tip part with an illuminating window and an observing window for observing an object illuminated by the illuminating light emitted from this illuminating window and a plurality of sheaths selectively and removably connected to the endoscope. The insertable part can be internally inserting when connected to the endoscope.

In the present invention, the plurality of sheaths are selectively removably fitted to the endoscope and are respectively different in the removably fitting function by which the endoscope can be used in a wide range of uses.

BRIEF DESCRIPTION OF THE DRAWINGS

FIGS. 1 to 21 relate to the first embodiment of the present invention;

FIG. 1 is an explanatory view of a whole endoscope system;

FIG. 2 is a view as seen in the direction A-A' indicated by the arrows in FIG. 1;

FIG. 3 is an explanatory view showing the internal formation of an endoscope;

FIG. 5 is a partly sectioned view of the tip part of a reinforcing sheath;

FIG. 6 is a formation explaining view of a sheath formed of an interlocked type spiral tube;

FIG. 7 is a sectioned view of the interlocked type spiral tube;

FIG. 8 is a partly sectioned view of the tip part of a sheath fitted with a curving device;

FIG. 9 is a partly sectioned view of the operating part of a sheath fitted with a curving device;

FIG. 10 is a sectioned view as seen in the direction B-B' indicated by the arrows in FIG. 9;

FIG. 11 is a sectioned view of a sheath fitted with a channel.

FIG. 12 is a sectioned view in the direction C-C' in FIG. 11;

FIG. 13 is a sectioned view of the tip part of a sheath fitted with a side viewing device;

FIG. 14 is a sectioned view in the direction D-D' in FIG. 13;

FIG. 15 is a sectioned view in the direction E-E' in FIG. 14;

FIG. 16 is a formation explaining view of a sheath fitted with a fixed brush;

FIG. 17 is a sectioned view of a sheath fitted with a grinding device;

FIG. 18 is a sectioned view in the direction F-F' in FIG. 17;

FIG. 19 is a sectioned view of a sheath fitted with a rotary hone;

FIG. 20 is a sectioned view as seen in the direction G-G' indicated by the arrows in FIG. 19;

FIG. 21 is a sectioned view as seen in the direction H-H' indicated by the arrows in FIG. 20;

FIG. 24 is an explanatory view of a sheath removably fitted with a sensor adapter and an endoscope;

FIG. 25 is a sectioned view of the tip part of the sheath;

FIG. 26 is a sectioned view as seen in the direction I-I' indicated by the arrows;

FIGS. 27 and 28 relate to the fifth embodiment of the present invention;

FIG. 27 is an explanatory view of a system in which a sheat and endoscope are electrically connecated with each other;

FIG. 28 is an explanatory view of an eyepiece part endoscope;

FIGS. 29 to 32 relate to the sixth embodiment of the present invention;

FIG. 29 is an explanatory view of an endoscope system provided with a sheath connected with the endoscope in the intermediate part;

FIG. 30 is a formation explaining view of a connecting means;

FIG. 31 is a positioning explaining view of the connecting means;

FIG. 32 is an explanatory view of a C-ring;

FIGS. 33 to 37 relate to the seventh embodiment of the present invention;

FIG. 33 is a sectioned view of the tip part of a sheath having a side viewing adapter connected with the endoscope in the tip part;

FIG. 34 is a sectioned view as seen in the direction J-J' indicated by the arrows in FIG. 33;

FIG. 35 is a sectioned view of a sheath as fitted with no side viewing adapter;

FIG. 36 is a sectioned view as seen in the direction K-K' indicated by the arrows in FIG. 35;

FIG. 37 is an elevation of a sheath;

FIGS. 38 to 58 relate to the eighth embodiment of the present invention;

FIG. 38 is a block diagram of an electronic endoscope apparatus;

FIG. 39 is a formation view of an endoscope apparatus;

FIG. 41 is an explanatory view relating to the connection of a connector and light source apparatus;

FIG. 42 is an appearance view of a C-ring;

FIG. 43 is an explanatory view relating to the connectability of a connector and receptacle;

FIG. 44 is an explanatory view relating to the connectability of a connector and receptacle;

FIG. 45(A)-45(B) are explanatory views of a modification of a discriminating means;

FIG. 47 is an explanatory view relating to the connectability of a connector and receptacle;

FIG. 48 is an explanatory view of a modification of a discriminating means;

FIG. 50 is a explanatory view relating to the connection of a connector and light source apparatus;

FIG. 51 is an explanatory view relating to the connectability of a connector and light source apparatus;

FIG. 52(A)-52(C) are explanatory views relating to the connection of a connector and receptacle;

FIG. 53 is an explanatory view relating to the connectability of a connector and receptacle;

FIG. 55 is an explanatory view of a discriminating means;

FIG. 56 is an explanatory view relating to the discriminating means;

FIG. 57 is an explanatory view relating to an inserting hole formation;

FIG. 58 is an explanatory view relating to lighting a light source.

DETAILED DESCRIPTION OF THE PREFERRED EMBODIMENTS OF THE INVENTION

Figure 1:
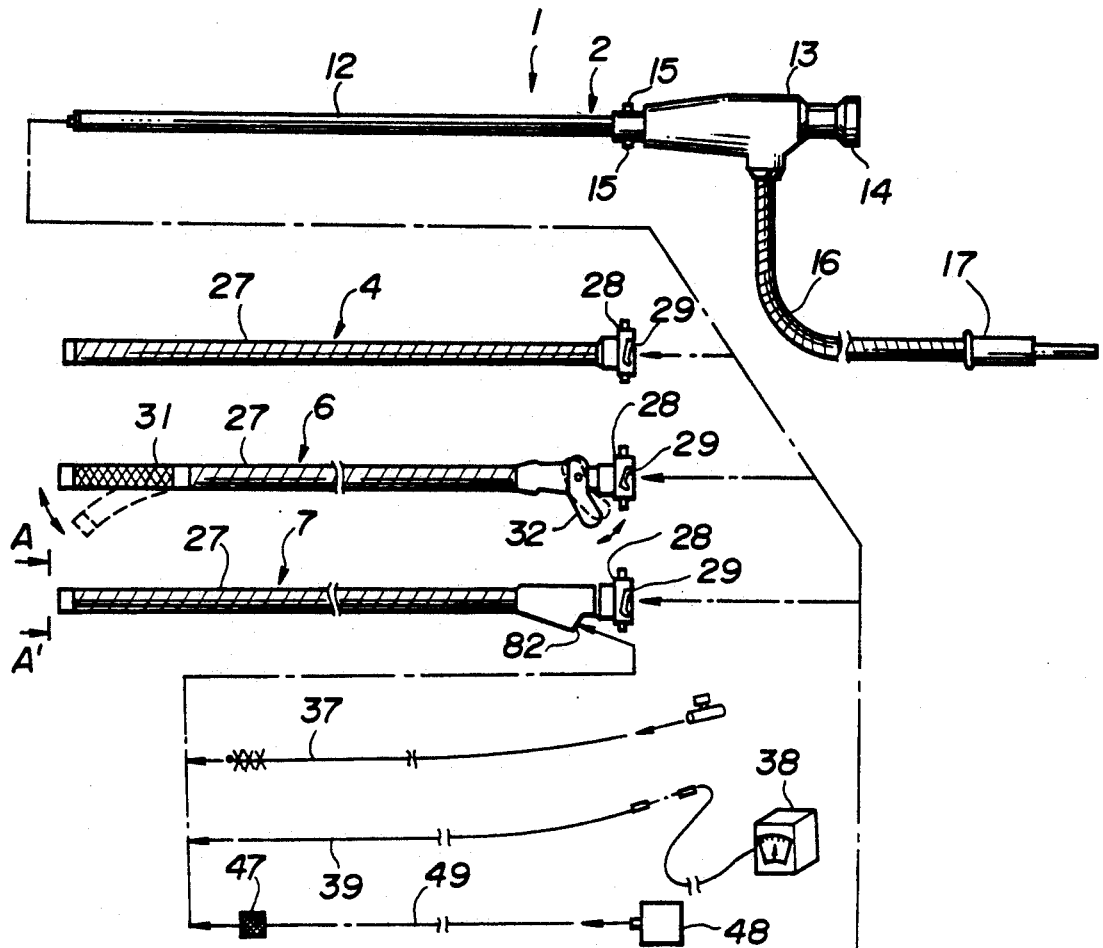
Figure 2:
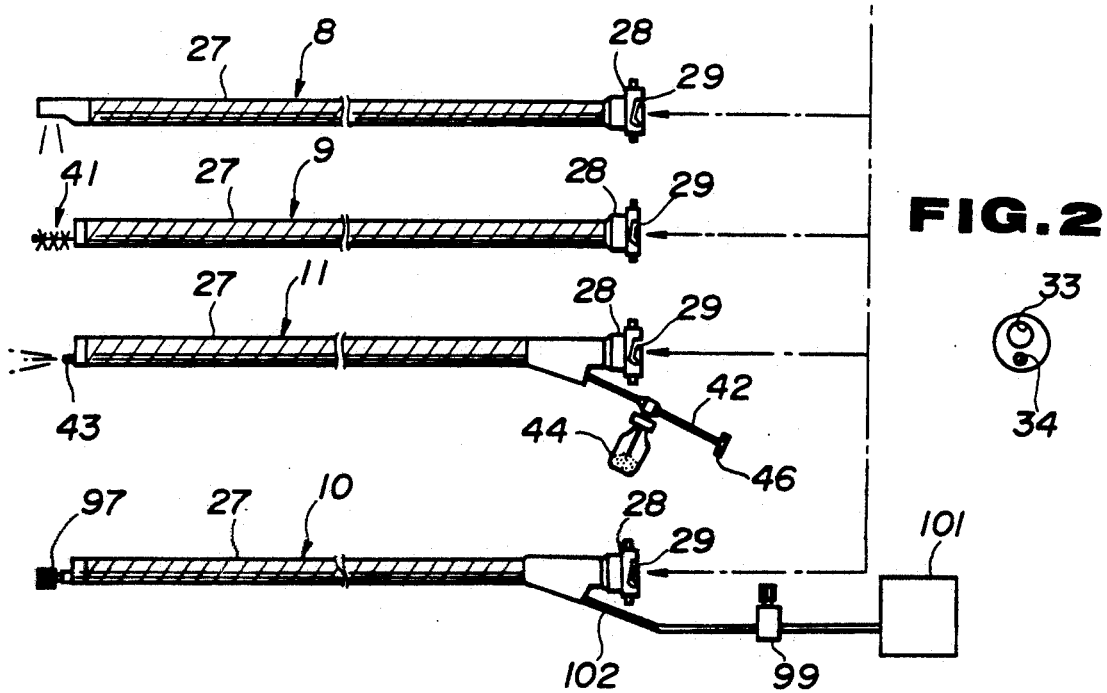

An endoscope system 1 in the first embodiment of the present invention comprises a fiber scope 2, a light source apparatus 3 for feeding an illuminating light to this fiber scope 2 and a sheath group consisting of a plurality of sheaths removably connected to the fiber scope 2.

In this embodiment, the sheath group consists of a reinforcing sheath 4, a curving device fitted sheath 6, a channel fitted sheath 7, a side viewing device fitted sheath 8, a fixed brush fitted sheath 9, a rotary hone fitted sheath 10 and a grinding device fitted sheath 11.

The above mentioned fiber scope 2 is provided with a thick operating part 13 connected to the rear end part of a flexible insertable part 12 formed of a resin the outer surface, an eyepiece 14 in the rear end part of this operating part 13 and a light guide hose 16 extended from the side of the operating part 13. A connector 17 provided at the rear end of this light guide hose 16 is removably connected to the above mentioned light source apparatus 3. By the way, sheath connecting pins 15 are provided to project in the diametral direction at the front end of the operating part 13.

Figure 3:
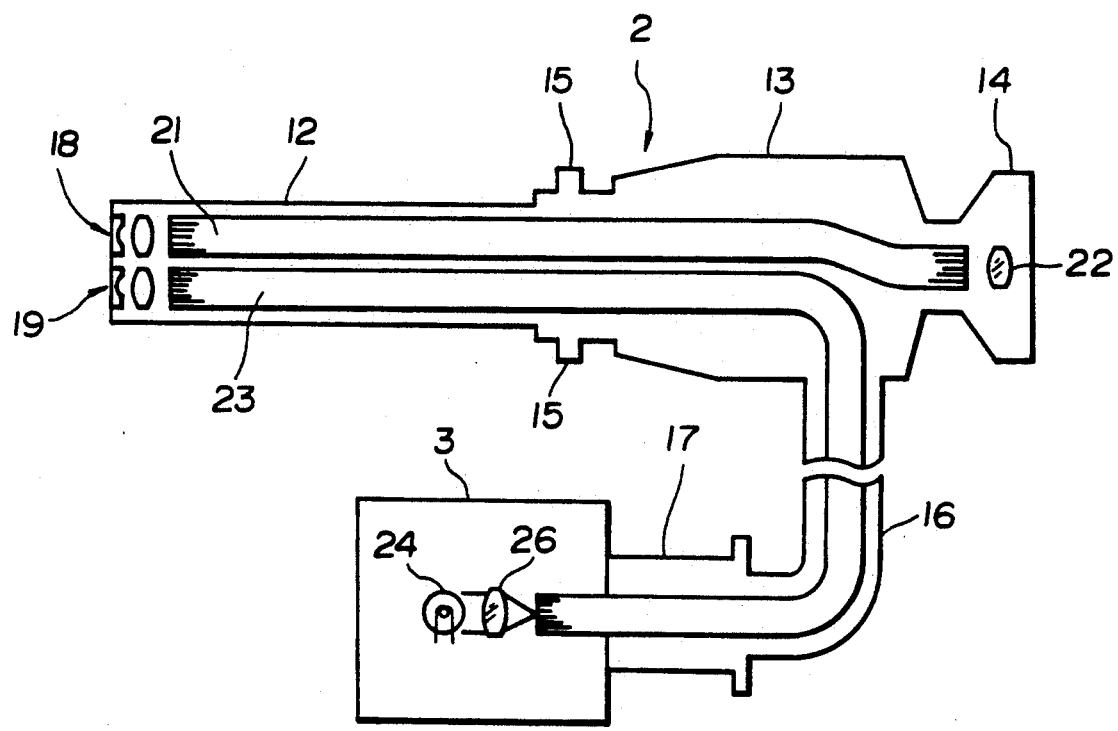

In FIG. 3, the above mentioned insertable part 12 is provided at the tip with an objective lens system 18 as an observing window and a light distributing lens system 19 as an illuminating window. The entrance end surface of an image guide 21 formed of a fiber bundle is provided in the image forming position of the objective lens system 18. The image guide 21 is inserted through the insertable part 12 and operating part 13 and is led to the eyepiece 14 so that an optical image transmitted through the image guide 21 may be observed with a naked eye through an eyepiece lens 22.

The exit end surface of a light guide 23 formed of a fiber bundle is provided in the rear of the light distributing lens system 19. This light guide 23 is inserted through the insertable part 12, operating part 13 and light guide hose 16 and is led to the connector 17 so that, when the connector 17 is connected to the light source apparatus 3, an illuminating light output from a light source 24 provided within the light source apparatus 3 and condensed by a condenser lens 26 will be radiated on the entrance end surface of this light guide 23.

Figure 7:
Figure 5:
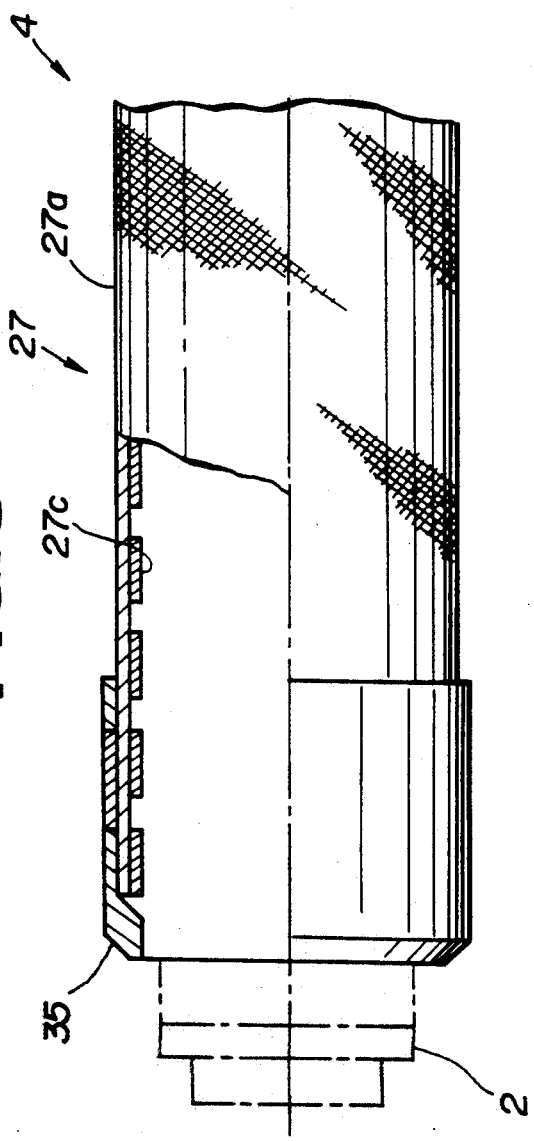

The above mentioned reinforcing sheath 4 is to protect the insertable part 12 formed of a resin and consists of a tubular sheath body 27 having an inside diameter through which the above mentioned insertable part 12 can be inserted as, for example, of a metal blade 27a shown in FIG. 5 or an interlocked type spiral tube 27b shown in FIG. 7 and a connecting part 28 provided at the rear end of this sheath body 27 and to be connected to the operating part 13.

Figure 4A:
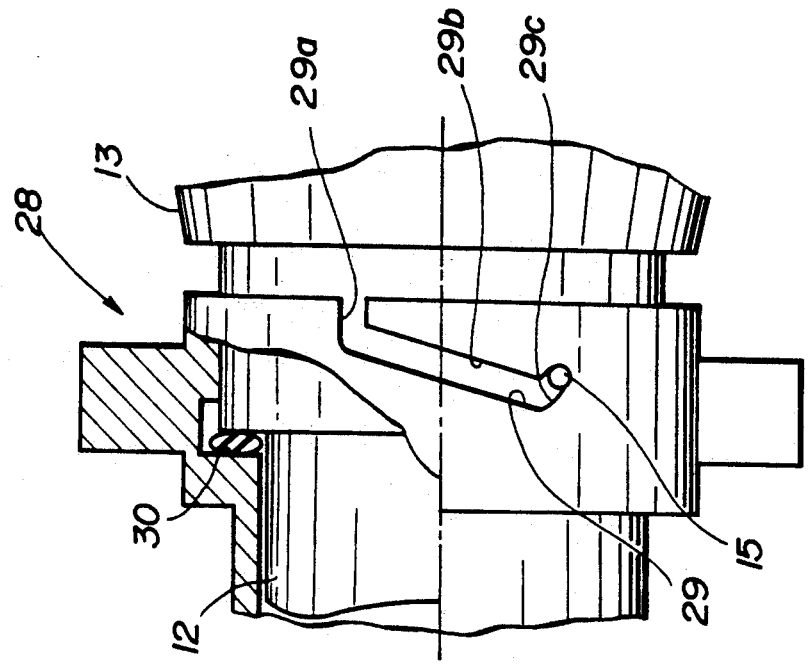
FIGS. 4(A) and 4(B) are partly sectioned views of a connecting means.
Figure 4B:
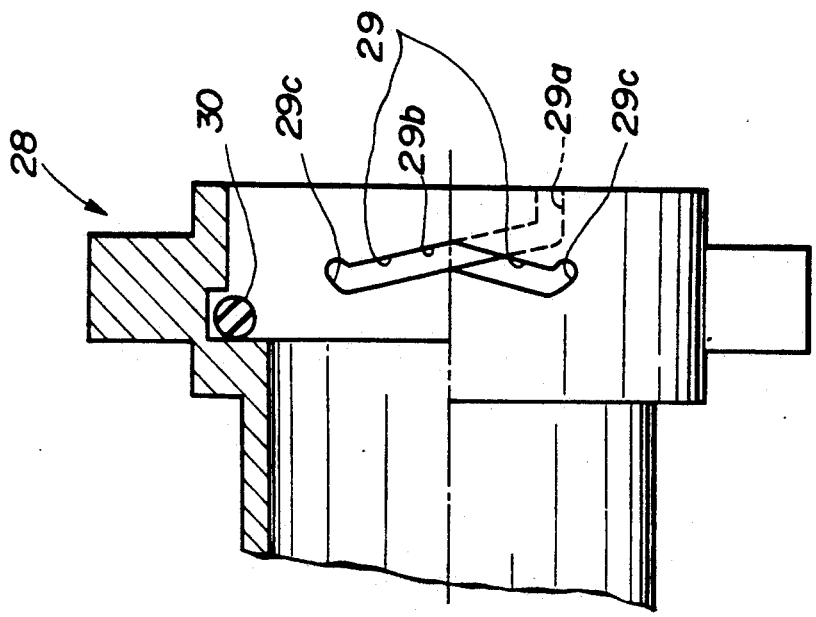

The above mentioned connecting part 28 is provided with cam grooves 29 near such inserting port into which the fiber scope 2 is to be inserted as is shown in FIGS. 4(A) and 4(B) and is fitted with an O-ring 30 on the inner peripheral surface of the inserting port. The above mentioned cam groove 29 is formed of a longitudinal groove 29a provided in the lengthwise direction of the sheath 4, a first inclined groove 29b continued to the longitudinal groove 29a and inclined to the lengthwise direction of the sheath 4 and a second inclined groove 29c inclined in the direction reverse to the first inclined groove 29b. By the way, in case the fiber scope 2 is to be fitted to the thus formed connecting part 28, when the insertable part 12 is inserted through the sheath 4 and the pin 15 is put into the longitudinal groove 29a and is led to the first inclined groove 29b, the operating part 13 or connecting part 28 will be rotated. When rotated, the pin 15 will proceed along the first inclined groove 29b so that the operating part 13 at the end will press and transform the O-ring 30. The pin 15 will drop into the second inclined groove 29c from the first inclined groove 29b and will be engaged within the second inclined groove 29c by the energizing force generated when the O-ring 30 is transformed. In case the fiber scope 2 is to be removed from the connecting part 28, when the operating part 13 is pushed against the connecting part 28 side and the operating part 13 or connecting part 28 is rotated in the direction reverse to fitting, thereby the pin 15 will be removed from the second inclined groove 29c and will be removed from the connecting part 28 through the first inclined groove 29b and longitudinal groove 29a.

By the way, FIG. 5 shows the sheath body 27 formed of the metal blade 27a.

Figure 6:
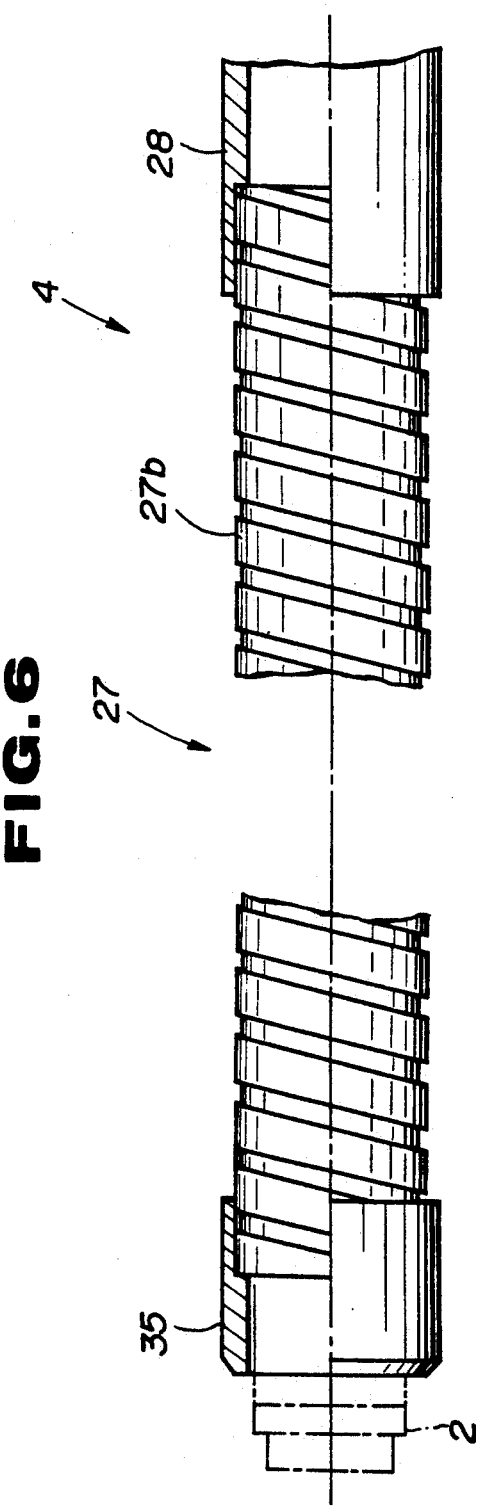

In FIG. 5, the inner layer of the sheath body 27 is a flex 27c made of a band-like plate member as spirally wound like a pipe. This flex 27c is coated on the outer periphery with a metal blade 27a knitted of fine metal wires. The sheath body 27 is externally fitted at the tip with a ring-like mouthpiece 35 fixed as by soldering to the sheath body 27. FIG. 6 shows the sheath body 27 formed of the interlocked type spiral tube 27b. This interlocked type spiral tube 27b is formed of such member as, for example, a metal so as to be of such cross-section as is shown in FIG. 7, and is curvable.

By the way, in case the fiber scope 2 is fitted with the reinforcing sheath 4, the insertable part 12 of the fiber scope 2 will be exposed at the tip out of the mouthpiece 35.

The above mentioned curving device fitted sheath 6 is provided with a curvable part 31 on the tip side of the sheath body 27 so that, when a curving lever 32 provided on the connecting part 28 shown in FIG. 4 is rotated as shown by the broken line, the curvable part 31 will be able to be curved as shown by the broken line.

Figure 8:
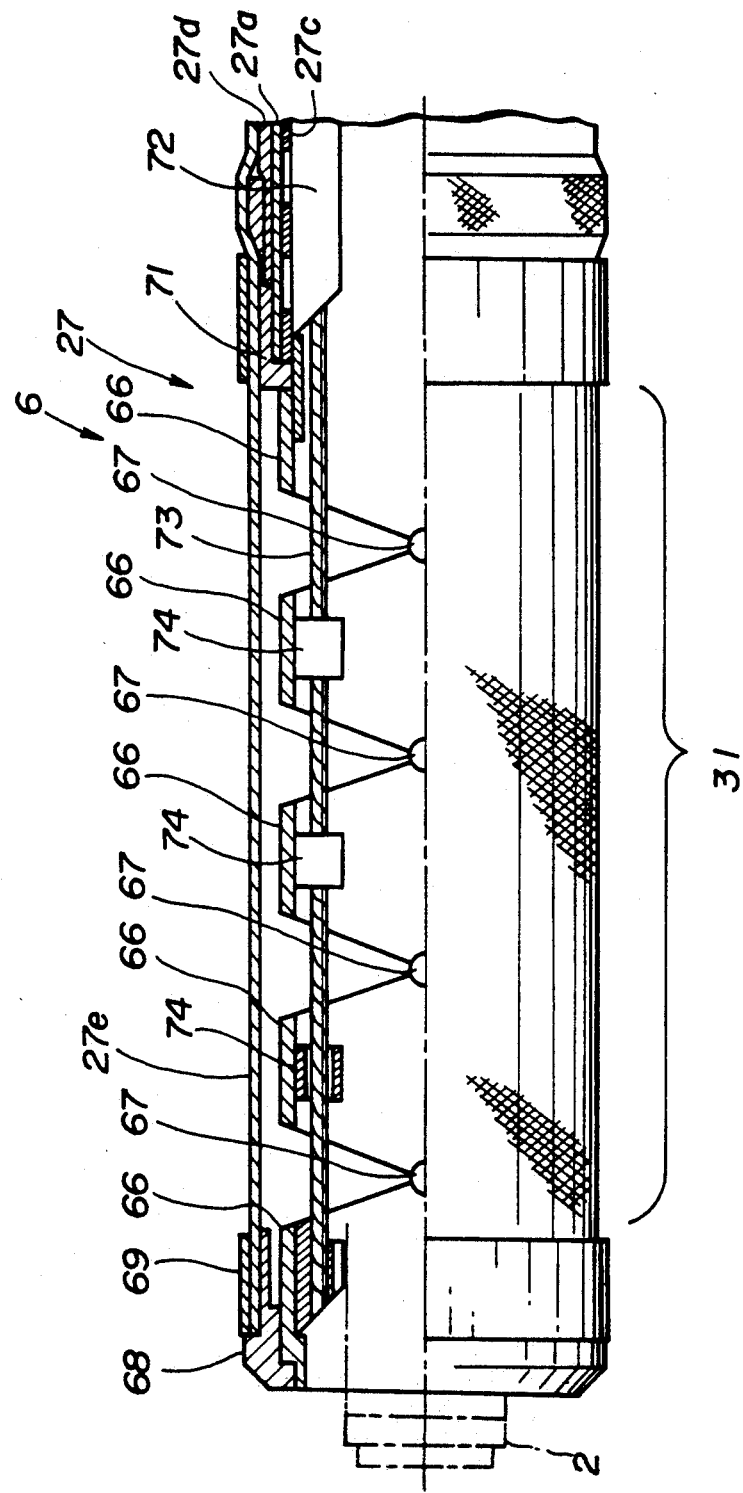
Figure 13:
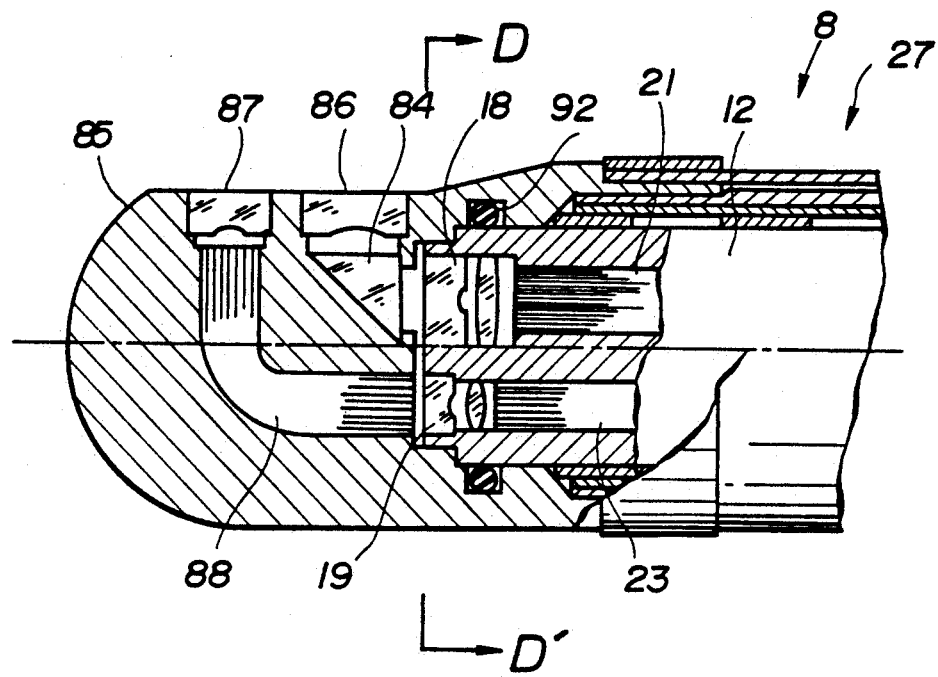
Figure 14:
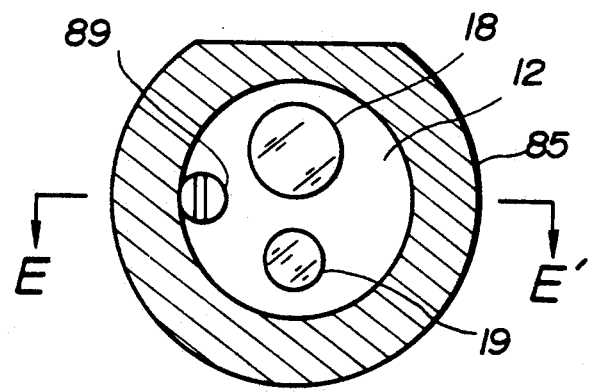
Figure 15:
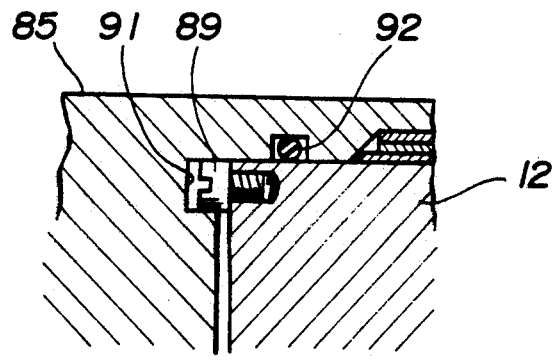

The above mentioned curvable part 31 is formed as in FIG. 8 and has a plurality of curving frames 66 rotatably connected with one another through pins 67. An outer blade receptacle 68 is externally fitted and fixed to the curving frame 66 located at the frontmost end and an outer blade 27e coating the curving frames 66 is fixed to this outer blade receptacle 68 with a fixing metal piece 69. The curving frame 66 located at the rearmost end is connected to the sheath body 27 coated with a flex 27c, metal blade 27a and resin coating 27d in the order from the innermost layer side through a hose mouthpiece 71. By the way, the above mentioned outer blade 27e coats the curvable part 31 and sheath body 27 on the outermost periphery.

Angle wires 73 inserted through angle pipes 72 are provided in the lengthwise direction of the sheath body 27 within the above mentioned sheath body 27. The angle pipes 72 lead at the tips to the tip of the sheath body 27. The angle wires 73 exposed out of the angle pipes 72 are guided by wire guides 74 provided on the inner peripheral surfaces of the curving frames 66 and are fixed as by soldering to the inner peripheral surface of the curving frame at the frontmost end so as to have an angle of substantially 180 degrees with each other.

The above mentioned curving lever 32 is formed as in FIGS. 9 and 10 in which the curving lever 32 is formed of a ring-like body 32 and a wire receiving part 32b and finger hanging part 32c provided to have an angle of 180 degrees with each other by projecting in the diametral direction out of the body part 32a. The connecting part 28 is inserted through the body part 32a. On the outer peripheral wall of the connecting part 28, the body 32a is rotatably supported by lever supporting pins 76 provided to project so as to have an angle of 180 degrees with each other. The above mentioned angle wires 73 inserted through the sheath body 27 and passed through the connecting part 28 are fixed as by soldering at the ends respective to the roots of the above mentioned wire receiving part 32b and finger hanging part 32c.

By the way, in case the fiber scope 2 is fitted with the curving device fitted sheath 6, the insertable part 12 of the fiber scope 2 will be exposed at the tip out of the outer blade receptacle 68.

As shown in FIG. 11, the above mentioned channel fitted sheath 7 is provided with a multilumen tube 78 provided with not only the scope inserting channel 33 for inserting the insertable part 12 through the sheath body 27 but also a channel 34. The metal blade 27a coating the multilumen tube 78 is fixed at the tip to this hose mouthpiece 80. A pipe-like tube receptacle 79 connected to the scope inserting channel 33 and a pipe-like channel mouthpiece 81 connected to the channel 34 are provided at the rear end of the multilumen tube 78.

The above mentioned multilumen tube 78 is connected at the rear end to the connecting part 28. The above mentioned tube receptacle 79 communicates with the inserting port for inserting the fiber scope 2 of the connecting part 28. The above mentioned channel mouthpiece 81 communicates with a treating instrument inserting port 82 provided in the connecting part 28. A brush 37 for cleaning or the like which can be, a sensor 39 connected, for example, to a voltage detecting meter 38 or the like and a flexible shaft 49 provided at the tip with a hone 47 so that, when connected with a motor 48, the hone 47 will be rotated and driven, so that it can be inserted through this treating instrument inserting port 82 which can be thus used for many purposes.

By the way, in case the fiber scope 2 is fitted with the channel fitted sheath 7, the insertable part 12 of the fiber scope 2 will be exposed at the tip out of the hose mouthpiece 80.

The above mentioned side viewing device fitted sheath 8 is provided with a tip body 85 at the tip of the sheath body 27. An objective lens 86 and light distributing lens 87 are provided on the outer peripheral wall surface of the tip body 85 so that the optical axis of the objective lens 86 may be bent by a prism 84 to coincide with that of the objective lens system 18 of the fiber scope 2 inserted through the sheath body 27. The light distributing lens 87 is positioned on the exit end surface side of the light guide 88 provided within the tip body 85 and molded to be bent by about 90 degrees. The optical axis of the entrance end surface of the light guide 88 coincides with that of the light distributing lens system 19 of the fiber scope 2.

By the way, a positioning pin 89 is screwed at the tip of the fiber scope 2 so that, when this pin 89 fits in a positioning recess 91 provided in the tip body 85, the respective optical axes of the sheath body 27 side prism 84 and the fiber scope 2 side objective lens system 18, and of the sheath body 27 side light guide 88 and the fiber scope 2 side light distributing lens system 19, will coincide with each other. Further, an O-ring 92 is fitted within the tip body 85 so as to maintain water-tightness, lest a liquid should come in between the tip of the fiber scope 2 and tip body 85.

Figure 16:
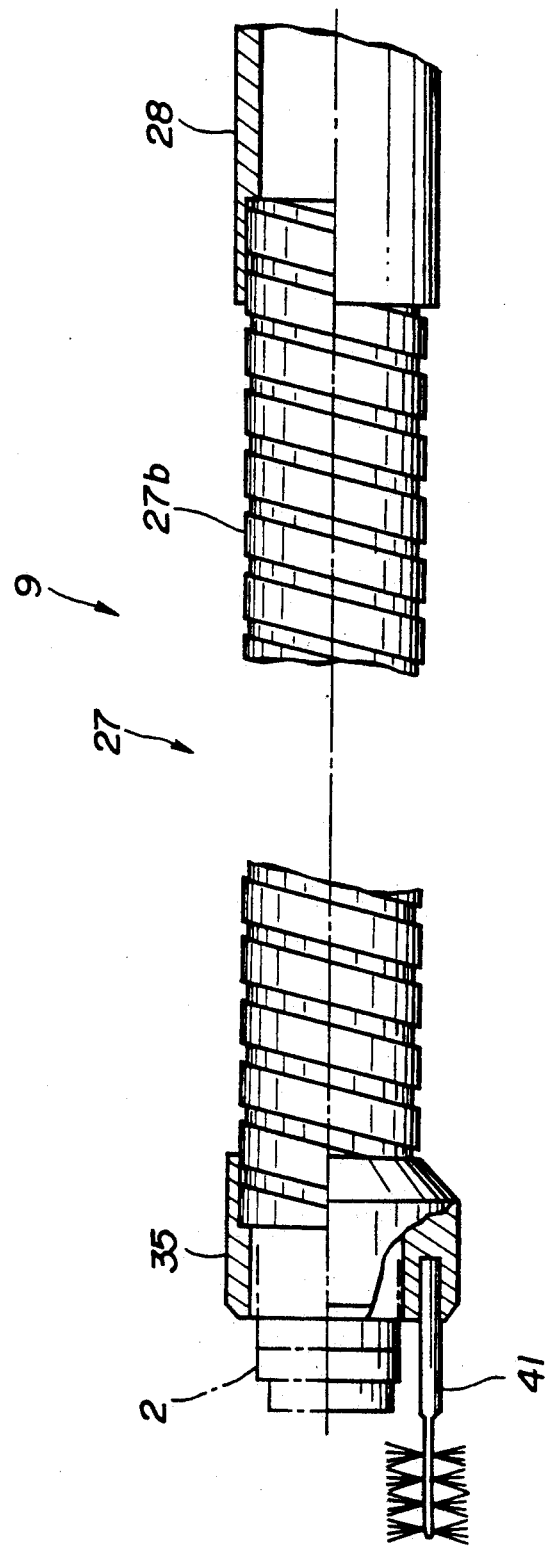

As shown in FIG. 16, the above mentioned fixed brush fitted sheath 9 is of substantially the same formation as of the reinforcing sheath 4 shown in FIG. 6. The difference is that the mouthpiece 35 is provided with a brush 41 for removing stains and aggregations of material, and projects in the tip direction so that, when this sheath 9 is operated to advance and retreat, the stains and aggregations will be removed with the brush 41.

By the way, in case the fiber scope 2 is fitted with the fixed brush fitted sheath 9, the insertable part 12 of the fiber scope 2 will be exposed at the tip out of the mouthpiece 35.

Figure 17:
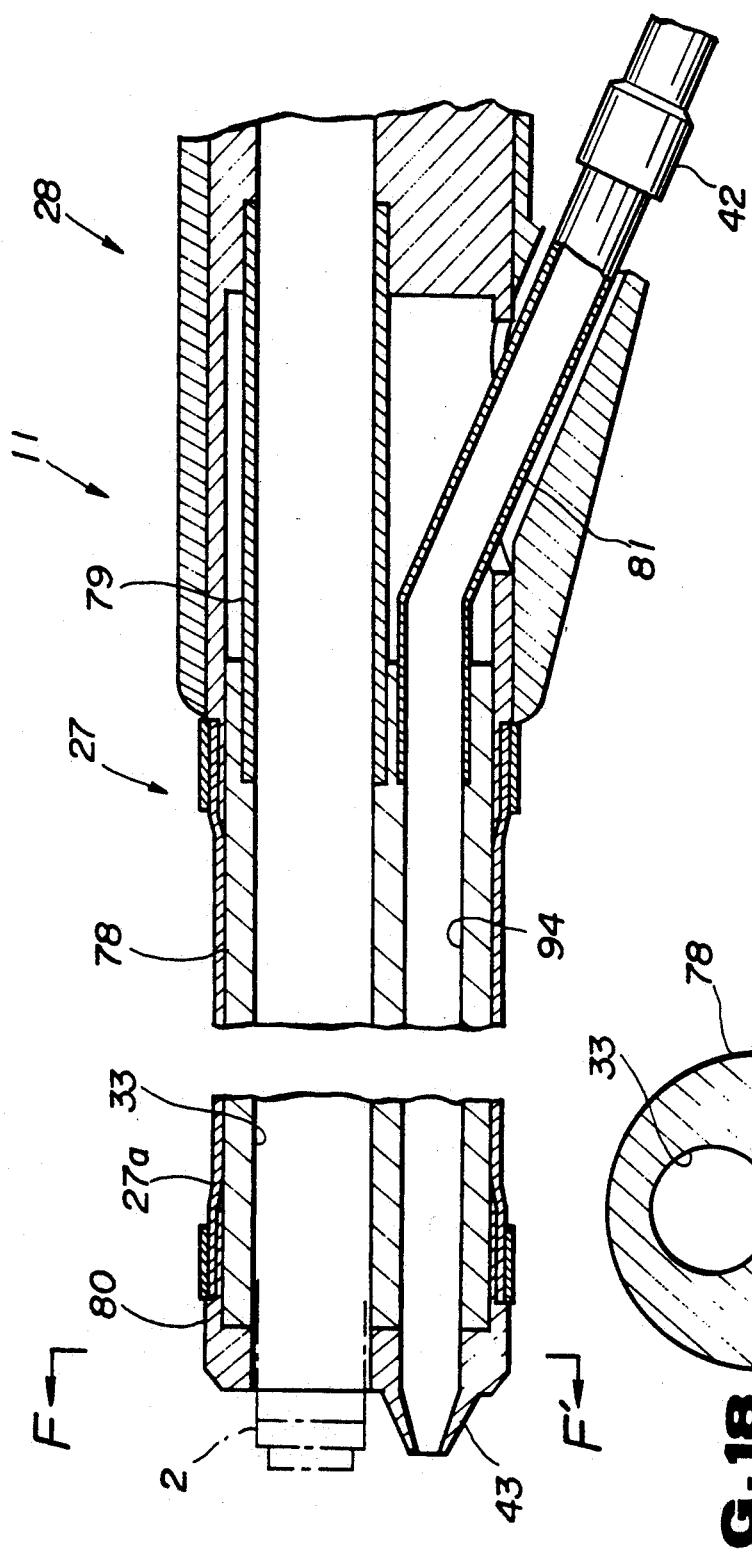
Figure 18:
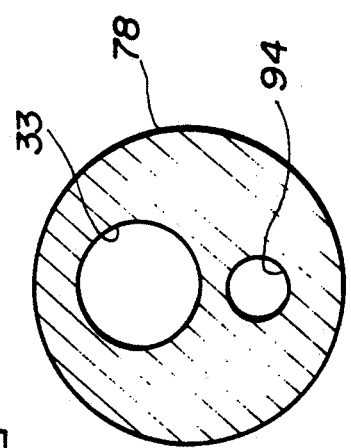

As shown in FIG. 17, the above mentioned grinding device fitted sheath 11 is of substantially the same formation as of the channel fitted sheath 7 shown in FIG. 11. The difference is that the treating instrument inserting channel 34 is a grinding material path 94 for transmitting a grinding material with compressed air and the hose mouthpiece 80 is provided with a jetting port 43 for jetting the grinding material by communicating with the grinding material path 94. Further, the channel mouthpiece 81 connected to the grinding material path 94 projects out of the connecting part 28 and a tube for transmitting the grinding material with high pressure air is connected to this projecting part. This tube 42 is provided in the intermediate part with a container 44 containing the grinding material and at the rear end with a joint 46 which can be connected with a high pressure air source.

By the way, in case the fiber scope 2 is fitted with the grinding device fitted sheath 11, the insertable part 12 of the fiber scope 2 will be exposed at the tip out of the hose mouthpiece 80.

Figure 19:
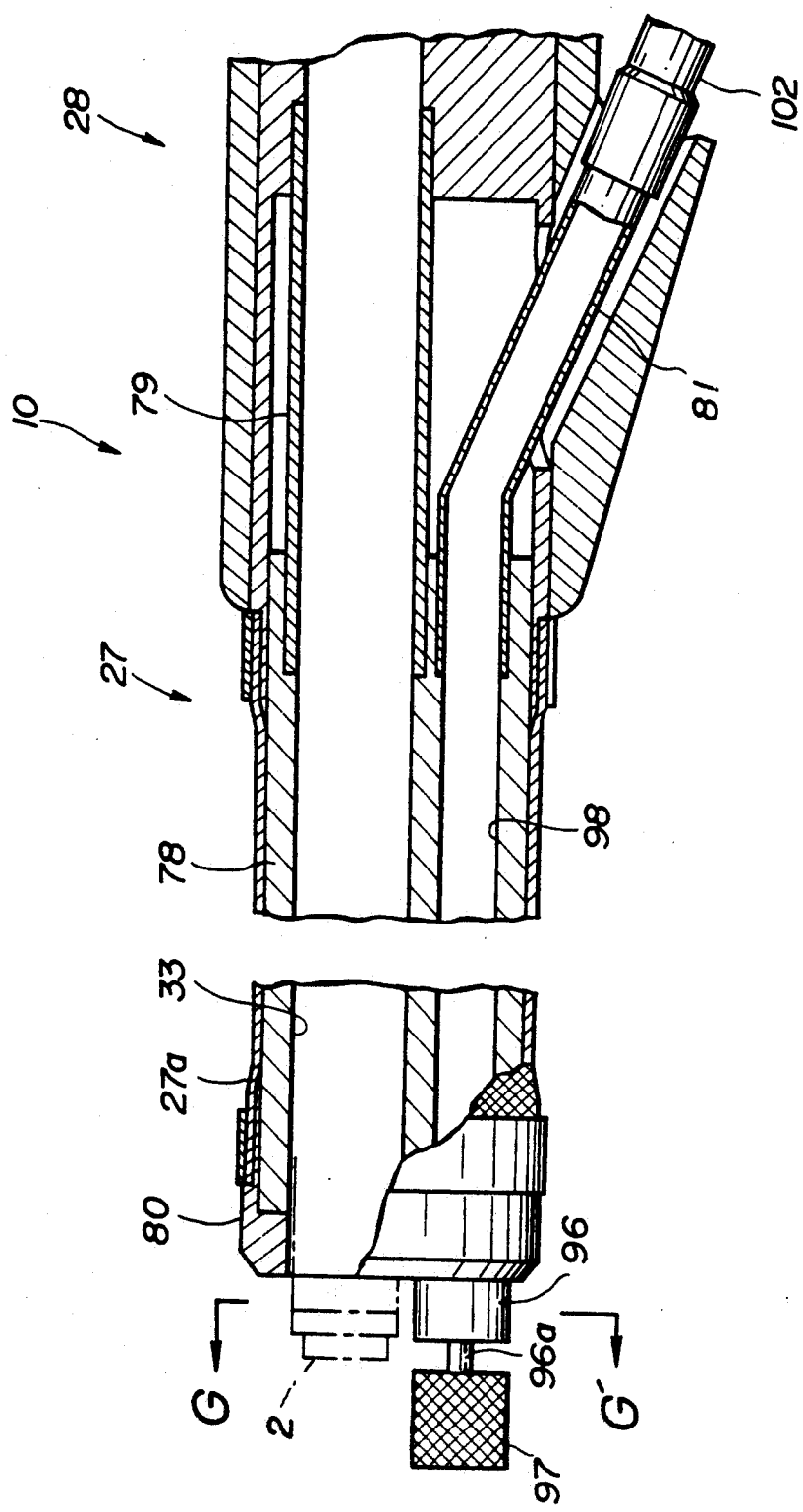

As shown in FIG. 19, the above mentioned rotary hone fitted sheath 10 is of substantially the same formation as of the grinding device fitted sheath 11 shown in FIG. 17. The difference is that a hone driving vane type air motor 96 is provided in place of the jetting port 43 and a hone 97 is fixed to a driving shaft 96 projecting toward the tip of this air motor 96. Further, the grinding material path 94 is a compressed air path 98 for transmitting compressed air to the air motor 96. The channel mouthpiece 81 is connected by a tube 102 to a compressor 101 through an air volume regulating apparatus 99.

By the way, in case the fiber scope 2 is fitted with the rotary hone fitted sheath 10, the insertable part 12 of the fiber scope 2 will be exposed at the tip out of the hose mouthpiece 80.

Figure 20:
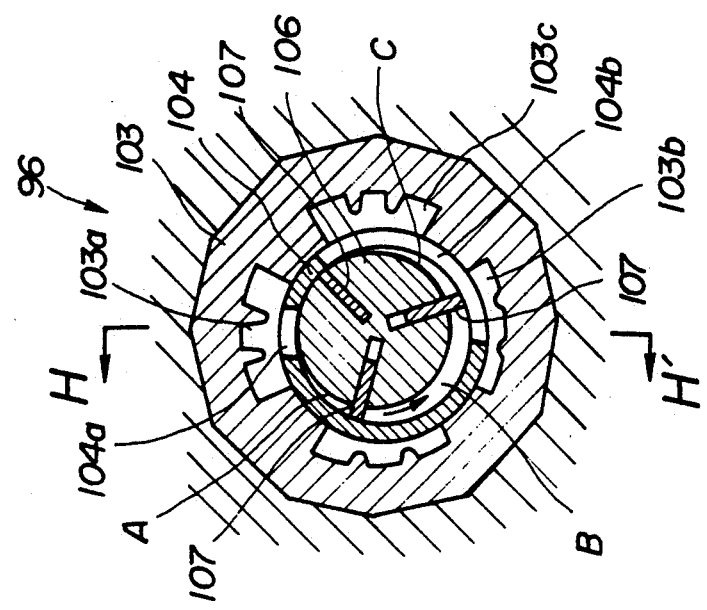
Figure 21:
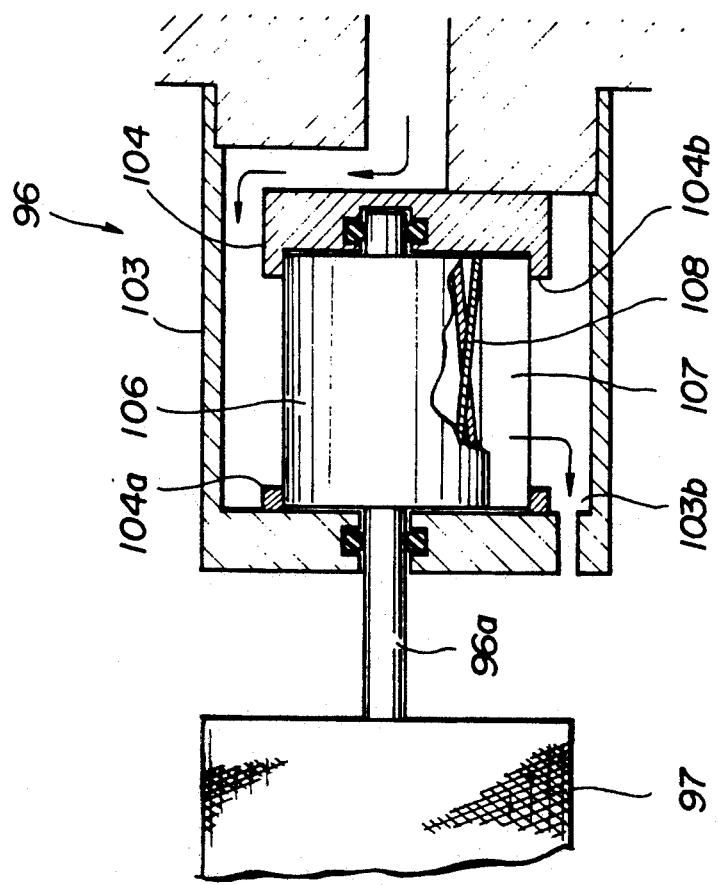

The above mentioned air motor 96 is formed as shown in FIGS. 20 and 21.

The air motor 96 is provided with a rotor supporting block 103 within which a cylindrical rotor supporting tube 104 is provided. The rotor supporting tube 104 is provided with an air feeding port 104a and air discharging port 104b. The rotor supporting block 103 is provided in the position corresponding to the air feeding port 104a with an air feeding path 103a communicating with the above mentioned compressed air path 98 and in the position corresponding to the air discharging port 104b with air discharging paths 103b and 103c. A rotor 106 is eccentrically borne within the rotor supporting tube 104 and is provided in the diametral direction with, for example, three vanes 107 so as to be pressed against the inner peripheral surface of the rotor supporting tube 104 by plate springs 108. The vanes 107 form air chambers A, B and C between the rotor supporting tube 104 and rotor 106.

In the above mentioned vane type air motor 96, when compressed air is fed into the air feeding port 104a from the compressed air path 98, the air will expand within the air chamber A and will rotate the rotor 106 counter-clockwise. When the rotor 106 is rotated, the air within the air chamber B will be discharged out of the air discharging port 104b through the air discharging path 103b to blow away chips or the like produced by grinding with the hone 97.

The operation of the endoscope system 1 formed as mentioned above shall be explained.

In the case of inspecting the interior of an engine or the like, the fiber scope 2 is fitted with the reinforcing sheath 4, lest the insertable part 12 formed of a resin or the like contact on the outer surface with a wall or projection within the engine and be thereby hurt or worn. In fitting, the insertable part 12 is inserted into the sheath 4, the pin 15 provided on the operating part 13 is engaged with the cam groove 29 and the connecting part 28 is rotated to connect the fiber scope 2 and reinforcing sheath 4 with each other.

On the other hand, the light guide hose 16 is connected to the light source apparatus 3 to feed the fiber scope 2 with the illuminating light from the light source apparatus 3.

The operator grips the operating part 13 and inserts the insertable part 12 fitted with the reinforcing sheath 4 into the engine. The illuminating light fed from the light source apparatus 3 is transmitted through the light guide 23 and is radiated to a part to be observed from the light distributing lens system 19. The reflected light from the observed part is made by the objective lens system 18 to form an image as an object image on the entrance end surface of the image guide 21. This object image is transmitted to the eyepiece lens 22 through the image guide 21 and is observed with the eyepiece 14.

In case the observing range is to be expanded, the curving device fitted sheath 6 is fitted to the fiber scope 2.

The prior fitted reinforcing sheath 4 is removed from the fiber scope 2 by rotating the connecting part 28 and the curving device fitted sheath 6 is fitted to the fiber scope 2 in the same manner as is mentioned above.

When the finger hanging part 32c of the curving lever 32 of the curving device fitted sheath 6 is pulled, one of the angle wires 73 fixed to the lever 32 will be pulled, the other will be relaxed and the curving part 31 will be curved as shown by the broken line in FIG. 1.

By the curing operation, the illuminating direction and visual field direction can be changed so that any desired part may be observed.

By the way, in this embodiment, the insertable part 12 of the fiber scope 2 has no curving function. If a scope having a curving function and this curving device fitted sheath 6 are used together, the whole will be formed as of curving in two steps so that the observing range may be expanded.

In order to clean the observed part, to collect samples, to recover foreign matters or to examine the environment, the channel fitted sheath 7 is fitted to the fiber scope 2 in the same manner as is mentioned above by rotating the connecting part 28 of the sheath 7 to engage the pin 15 of the operating part 13 with the cam groove 29.

In the case of cleaning, the brush 37 is inserted from the treating instrument inserting port 82, is projected out of the tip of the sheath 7, is pressed against the part to be cleaned and is advanced and retreated or rotated at the rear end. In the case of measuring the voltage of the observed part, a voltage detecting meter 38 is connected to a sensor 39 inserted through the channel 34 and the sensor 39 is projected at the tip out of the channel 34 to contact the measured part.

In the case of honing, a hone 47 is used. A flexible shaft 49 connected to the hone 47 is inserted into the channel 34 from the tip side of the sheath 7 and a motor 48 is connected to the flexible shaft 49 projected out of the treating instrument inserting port 82. Then, the motor 48 is driven with the hone in contact with the part to be ground. The grinding manner can be observed with the fiber scope 2.

By the way, not only the voltage detecting sensor, but also a pressure, temperature or sound sensor may be inserted. Also, though not illustrated, if a catheter is inserted through the channel 34, samples will be able to be collected or foreign matter will be able to be recovered.

In the case of an observation sidewise from the fiber scope 2 inserting direction, the side viewing device fitted sheath 8 is fitted to the fiber scope 2 in the same manner as is mentioned above by rotating the connecting part 28 of the sheath 8 to engage the pin 15 of the operating part 13 with the cam groove 29.

When the side viewing device fitted sheath 8 is fitted and the positioning pin 89 fits in the recess 91, the respective optical axes of the visual field converting optical system formed of the objective lens 86 and prism 84 and the objective lens system 18 and of the light distributing lens 87 and light distributing lens system 19 will coincide with each other to make an optical connection. When the side viewing device fitted sheath 8 is fitted, the manner in the direction intersecting at right angles with the sheath 8 inserting direction will be able to be observed from the eyepiece 14 of the fiber scope 2.

In the case of only cleaning the observed part, the fixed brush fitted sheath 9 is fitted in the same manner as is mentioned above by rotating the connecting part 28 of the sheath 9 to engage the pin 15 of the operating part 13 with the cam groove 29.

In cleaning, while being observed from the eyepiece 14, the brush 41 is led to the part to be cleaned and the entire scope 2 is operated to advance and retreat.

In the case of grinding, the grinding device fitted sheath 11 is fitted to the fiber scope 2 in the same manner as is mentioned above by rotating the connecting part 28 of the sheath 11 to engage the pin 15 of the operating part 13 with the cam groove 29. When a high pressure air source is connected to the joint 46 at the rear end of the tube 42 and high pressure air is fed in, the grinding material within the container 44 will be sucked out by the high pressure air, will be jetted at a high speed out of the jetting port 43 and will collide at a high speed with a part to be ground.

In the case of only grinding, the rotary hone fitted sheath 10 is fitted to the fiber scope 2 in the same manner as is mentioned above by rotating the connecting part 28 of the sheath 10 to engage the pin 15 of the operating part 13 with the cam groove 29. Compressed air is fed from a compressor 101 through an air volume regulating apparatus 99 from a tube 102 connected to the channel mouthpiece 81 and the air motor 96 provided at the tip of the sheath 10 is thereby rotated and driven to rotate the hone 97. The part to be ground is ground with the hone 97 in contact with it while being observed from the eyepiece 14 of the fiber scope 2.

As mentioned above, in this embodiment, as the connecting parts 28 of a plurality of sheaths 4, 6, 7, 8, 9, 10 and 11 different in their functions are of a common formation at one end, the above mentioned sheaths 4, 6, 7, 8, 9, 10 and 11 can be connected to one fiber scope 2 and therefore such economic disadvantage, that only one scope can be combined with one sheath as in the past, can be eliminated.

Also, as the scope having comparatively expensive optical parts built-in and the sheath formed of comparatively cheap mechanical parts and likely to be damaged are made separate from each other, in case the sheath is broken the repair cost will be low. As they have been integral, even in case the outer fitting is broken, the optical parts have been also replaced and the repair cost has been high.

By the way, a sheath in which the various functions described in this embodiment are combined or which has another function may be added to the present endoscope system.

Figure 22:
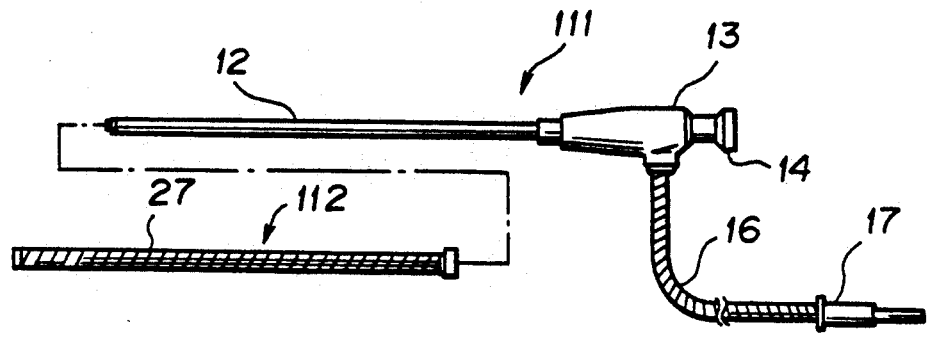
FIG. 22 relates to the second embodiment of the present invention and is an explanatory view of an endoscope system of a sheath length different from the length of the insertable part of the endoscope.

FIG. 22 shows the second embodiment of the present invention. By the way, the same component members as in the first embodiment shall bear the same reference numerals and shall not be explained here.

Whereas the respective sheaths, 4, 5, 7, 8, 9, 10 and 11 of the first embodiment are provided with connecting parts 28 for connecting with the fiber scope 2, this embodiment is formed of sheaths provided with no connecting part and a fiber scope.

The endoscope system of this embodiment comprises a fiber scope 111 provided with no pin 15, a reinforcing sheath 112 and a nonillustrated channel fitted sheath, fixed brush fitted sheath, rotary hone fitted sheath and grinding device fitted sheath.

The operating part 13 of the above mentioned fiber scope 111 is not provided with the sheath fitting pin 15. The reinforcing sheath 112 is of substantially the same formation as of the reinforcing sheath 4 shown in FIGS. 5 and 6 and the differences are that no connecting part 28 is provided and that the length of the insertable part 12 of the fiber scope 111 and the length of the sheath 112 do not coincide with each other. The above mentioned nonillustrated channel fitted sheath, fixed brush fitted sheath, rotary hone fitted sheath and grinding device fitted sheath are of the formations of the respective sheaths 7, 9, 10 and 11 from which the connecting parts 28 are removed but are otherwise the same.

In the case of using the reinforcing sheath 112 to observe the interior of an engine, the reinforcing sheath 112 is inserted, for example, into a spark plug hole and the insertable part 12 of the fiber scope 111 is inserted through the reinforcing sheath 112 inserted into this spark plug hole to that the insertable part 12 may be prevented from being damaged in case the insertable part 12 is inserted directly through the spark plug hole Also, in the case of using the above mentioned nonillustrated channel fitted sheath, fixed brush fitted sheath, rotary hone fitted sheath and grinding device fitted sheath, the sheath is gripped by hand at the operating part 13 side end to make respective operations. Thus, even in case the length of the sheath and the length of the insertable part 12 do not coincide with each other, the functions of the respective sheaths can be used.

The other formations, operations and effects are the same as in the first embodiment.

FIGS 23(A( to 23(C) show the third embodiment of the present invention. By the way, the same component members as in the first embodiment shall bear the same reference numerals and shall not be explained here.

Figure 23A:
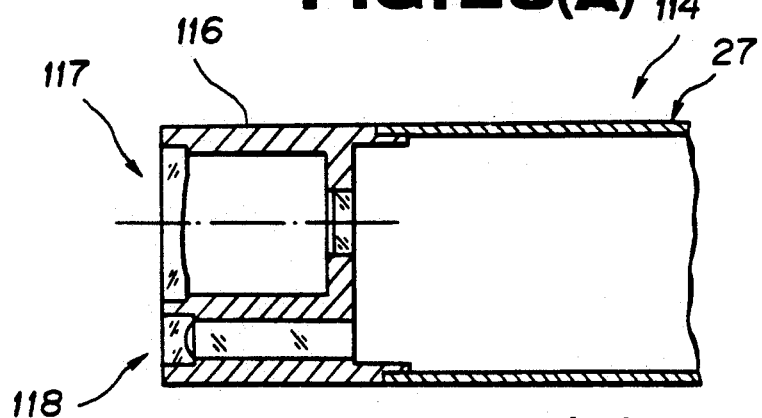
FIGS. 23(A) to 23(C) relate to the third embodiment of the present invention and are sectioned views of a sheath having an optical lens system.
Figure 23B:
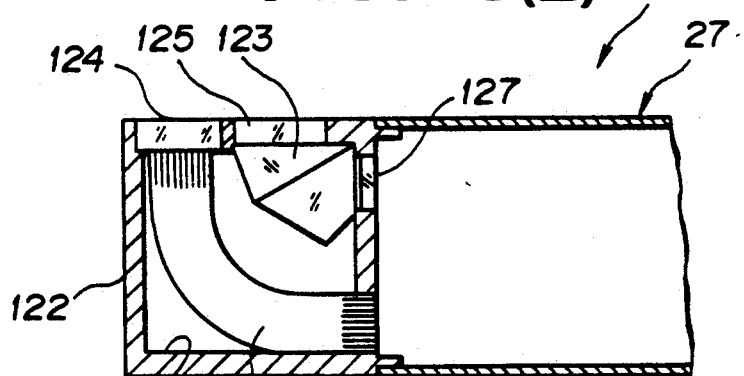
Figure 23C:
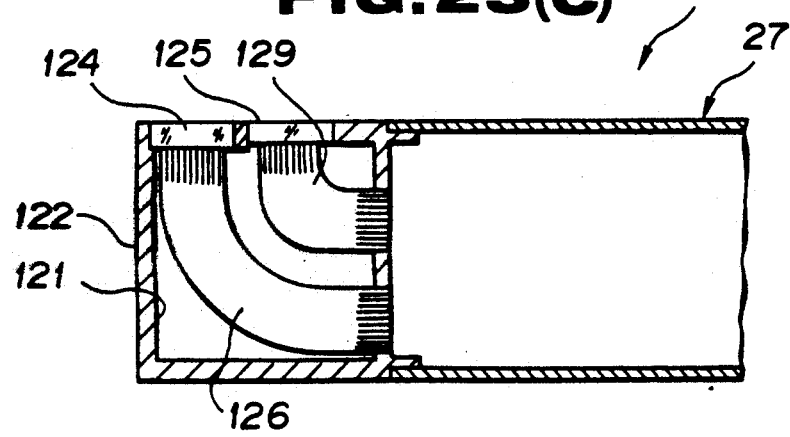

This embodiment is of an endoscope system provided with the sheaths shown in FIGS. 23(A) to 23(C) in addition to the respective sheaths, 4, 6, 7, 8, 9, 10 and 11 described in the first embodiment.

The sheath shown in FIG. 23(A) is a view angle changing sheath 114 in which the inserting direction is referred to as a visual field direction and the view angle of the visual field is changed. The sheaths shown in FIGS. 23(B) and 23(C) are both the same as the side viewing device fitted sheath 8 in function, but are different in formation.

The above mentioned view angle changing sheath 114 is provided at the tip of the sheath body 27 with a tip body 116 in which a view angle changing lens system 117 and an illuminating lens system 118 are provided so that the respective optical axes may be parallel with the lengthwise direction of the sheath 114. The optical axis of the view angle changing lens system 117 will coincide with the optical axis of the objective lens system 18 of the fiber scope 2 in case the sheath 114 is fitted to the fiber scope 2 and the optical axis of the illuminating lens system 118 will coincide with the optical axis of the light distributing lens system 19 of the fiber scope 2.

Also, a side viewing device fitted sheath 119 shown in FIG. 23(B) is provided at the tip of the sheath body 27 with a tip body 122 having an optical system housing part 121 within and on the outer peripheral wall surface of the tip body 122 with an observing cover glass 125 and illuminating cover glass 124. Within the housing part 121, a visual field direction changing prism 123 is provided as opposed to the observing cover glass 125 and the exit end surface of a light guide 126 is provided as opposed to the illuminating cover glass 124.

An observing cover glass 127 of an optical axis coinciding with the optical axis bend by the above mentioned prism 123 and the entrance end surface of the light guide 126 bent by about 90 degrees so as to be parallel with the lengthwise direction of the sheath 119 are provided on the connecting part 28 side end surface of the above mentioned tip body 122.

Further, a side viewing device fitted sheath 128 shown in FIG. 23(C) is provided with an image guide 129 bent by about 90 degrees in place of the prism 123 of the side viewing device fitted sheath 119 shown in FIG. 23(B) and the other formations are the same as in FIG. 23(C).

The other formations and operations are the same as in the first embodiment.

In this embodiment, as the view angle changing sheath 114 is added to the system, a wide range can be summarily observed and a narrow range can be observed in detail.

The other effects are the same as in the first embodiment.

Figure 24:
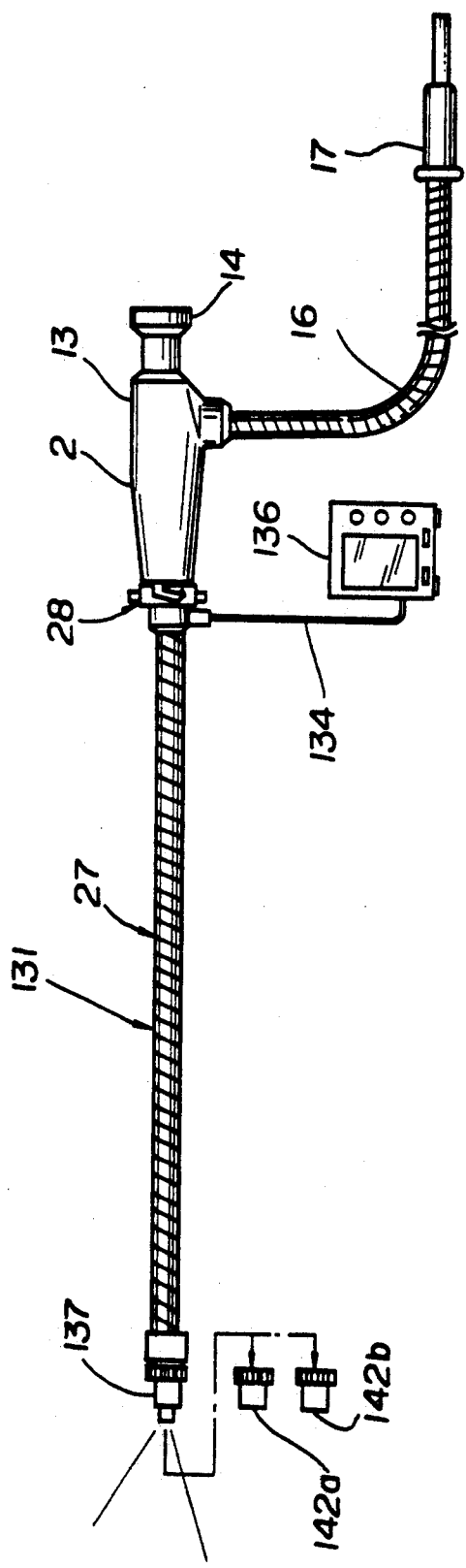
FIGS. 24 to 26 relate to the fourth embodiment of the present invention.
Figure 25:
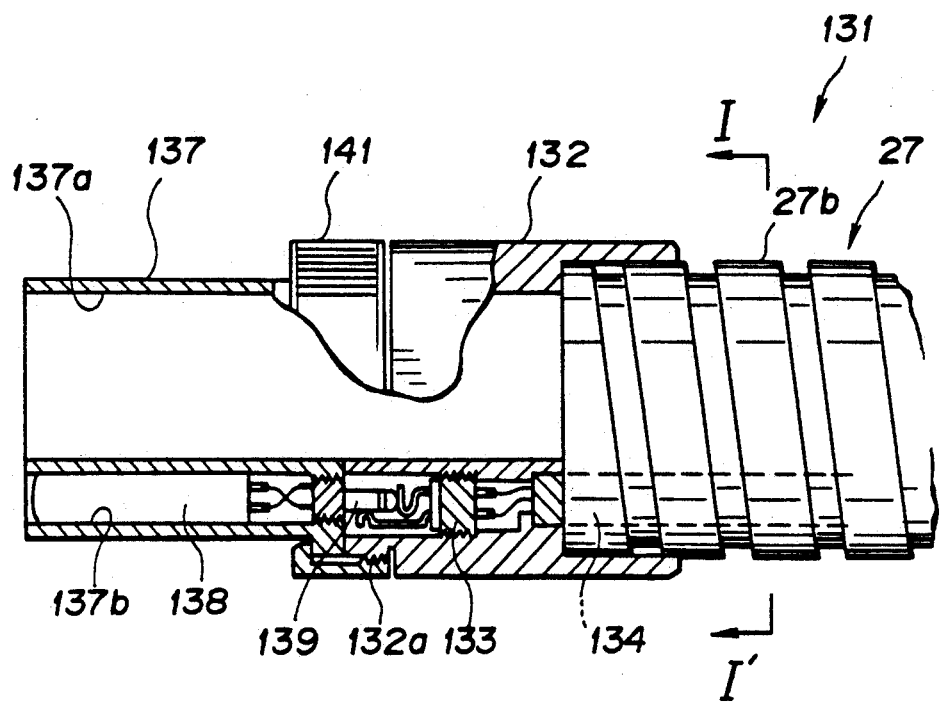
Figure 26:
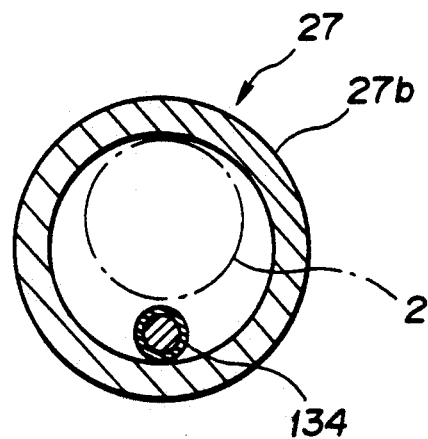

FIGS. 24 to 26 show the fourth embodiment of the present invention.

In this embodiment, a sensor sheath 131 is added to each of the sheaths 4, 6, 7, 8, 9, 10 and 11 shown in the first embodiment.

The sheath body 27 of the sensor sheath 131 is formed of the interlocked type spiral tube 27b of the cross-sectional shape shown in FIG. 7 and is provided at one end with the connecting part 28 and at the other end with a tip body 132. In the tip body 132, as shown in FIG. 25, a signal connector 133 is built-in and a signal cable 134 connected to the signal connector 133 is inserted through the sheath body 27, is extended out of the connecting part 28 and is connected to a sensor monitor 136.

The above mentioned tip body 132 is provided on the outer periphery of the tip with a male screw part 132 to which a sensor adapter 137 is to be screwed. The above mentioned sensor adapter 137 is provided with an inserting hole 137a for inserting the fiber scope 2 in case the sensor adapter 137 is fitted to the sensor sheath 131 and a sensor housing hole 137b. Any one sensor 138, for example, among a temperature sensor, humidity sensor, pressure sensor, gas ($O_2$, $CO_2$) sensor, radioactivity sensor and microphone is provided within the sensor housing hole 137. The above mentioned sensor 138 is connected to an electric contact 139 provided on the sheath side end surface of the adapter 137 so that, in case the adapter 137 is fitted to the sheath 131, the electric contact 139 will be connected to the above mentioned signal connector 133.

A connecting ring 141 is rotatably provided on the outer periphery at the rear end of the above mentioned sensor adapter 137 so that, when this connecting ring 141 is screwed to the male screw part 132 of the above mentioned tip body 132, the sensor adapter 137 will be fitted to the sensor sheath 131.

In this embodiment, if the sensor adapter 137 having, for example, a temperature sensor built-in is fitted to the sensor sheath 131, the temperature information detected by the temperature sensor will be output to the sensor monitor 136 through the signal cable 134 and the temperature will be displayed by a character or image in a monitor 136. Also, in case a sensor adapter 142a having a temperature sensor built-in, a sensor adapter 142b having a pressure sensor built-in or a sensor adapter having any other sensor built-in is fitted, the sensor monitor 136 will be changed to a monitor corresponding to each sensor for detection.

As mentioned above, in this embodiment in addition to the first embodiment, the state of such observing atmosphere as of the temperature, humidity, pressure, gas kind, radioactivity or sound can be investigated.

By the way, in case an electronic endoscope is to be used in place of the fiber scope 2, the information obtained from the sensor may be displayed in the monitor of the electronic endoscope.

Also, the sensor adapter 137 may be fitted to the curving device fitted sheath 6, channel fitted sheath 7, side viewing device fitted sheath 8, fixed brush fitted sheath 9, rotary hone fitted sheath 10 and grinding device fitted sheath 11 described in the first embodiment.

Further, a temperature measuring resistor, thermocouple, thermistor, semiconductor type and quartz crystal type are used for the above mentioned temperature sensor. A thermistor type, lithium chloride type, ceramic type, resistance type high molecular weight membrane type, capacity type high molecular weight type and crystal type are used for the humidity sensor. The pressure sensor is of a semiconductor type or piezoelectric device type. Further, the gas sensor is of a metal oxide semiconductor type, anion adsorptive oxidative gas (oxygen, nitrogen, oxide), cation adsorptive reductive gas ($H_2$, CO, CH, alcohol), iron oxide semiconductor type (town gas), zirconia type (oxygen) or galvanic type (oxygen). The radioactivity sensor is of a gas input counting tube, semiconductor type or scintillation type.

The other formations, operations and effects are the same as in the first embodiment.

FIGS. 27 and 28 show the fifth embodiment of the present inventin.

Whereas, in the above mentioned fourth embodiment, the sensor monitor 136 is connected to the sensor sheath 131, in this embodiment, the connecting part 28 and operating part 13 are electrically connected with each other so that the information obtained from the sensor may be displayed in the sensor monitor within the eyepiece 14.

In this embodiment, the sensor sheath 131 fitted to the fiber scope 2 is electrically connected with a sensor circuit not illustrated built-in in the operating part 13 through a signal cable 143 so that the obtained information may be output from the sensor circuit to a monitor 144 formed, for example, of an LED provided within the eyepiece 14 and may be observed together with an observed image 146.

The other formations are the same as in the fourth embodiment.

FIGS. 29 to 32 show the sixth embodiment of the present invention. By the way, the same component members as in the first embodiment shall bear the same reference numerals and shall not be explained here.

In this embodiment, the connecting part for connecting the sheath and fiber scope with each other is provided in the intermediate part of the sheath.

The endoscope system of this embodiment comprises a fiber scope 148, reinforcing sheath 154 and nonillustrated curving device fitted sheath, channel fitted sheath, side viewing device fitted sheath, fixed brush fitted sheath, rotary hone fitted sheath and grinding device fitted sheath.

Figure 30:
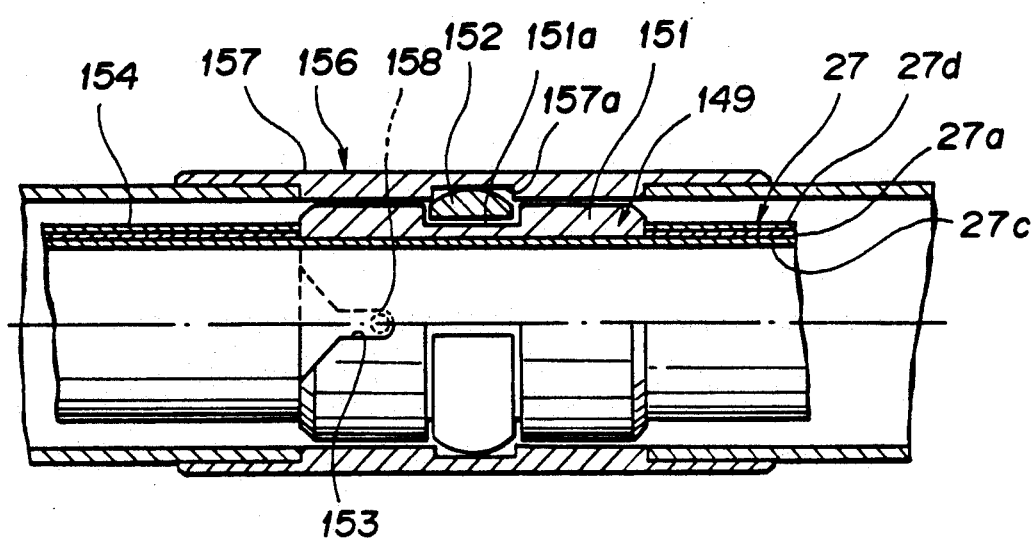
Figure 31:
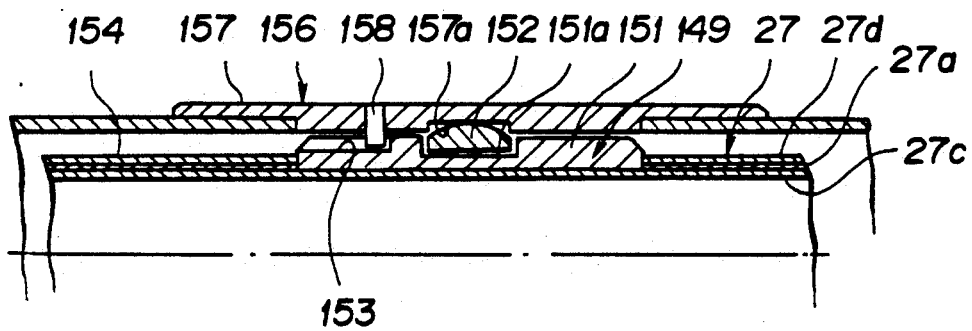
Figure 32:
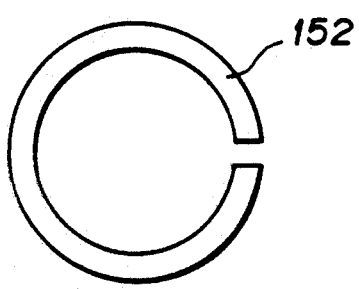

A scope side connecting part 149 is provided in the intermediate part of the insertable part 12 of the fiber scope 148 of this embodiment and is provided with a cylindrical connecting metal piece 151 fixed on a flex 27c forming the outer skin of the insertable part 2 as shown in FIGS. 30 and 31. A groove 151a is peripherally provided in the middle on the outer peripheral surface of the connecting metal piece 151 and a C-ring 152 shown in FIG. 32 is fitted in this groove 151. A positioning groove 153 is provided on the tip side of the outer peripheral surface of the connecting metal piece 151.

On the other hand, the reinforcing sheath 154 is provided in the middle of the sheath body 27 with a sheath side connecting part 156 which is provided with a cylindrical connecting cylinder 157 provided peripherally on the inner peripheral surface with a groove 157 in which the above mentioned C-ring 152 is to be fitted. A pin 158 is provided to project in the inside diameter direction on the tip side of the inner peripheral surface of the connecting cylinder 157 and is to be fitted in the above mentioned positioning groove 153 to position the sheath 154 and insertable part 12.

The other formations of the reinforcing sheath 154 are the same as in the first embodiment.

In this embodiment, in the case of fitting the reinforcing sheath 154 to the fiber scope 148, the insertable part 12 is inserted into the sheath 154 so that the pin 158 may engage with the positioning groove 153. When the connecting metal piece 151 of the insertable part 12 reaches the connecting cylinder 157, the C-ring 152 will be pressed and elastically transformed so as to become smaller in the outside diameter by the inner peripheral surface of the connecting cylinder 157. When it is further inserted until the C-ring 152 comes to the groove 157a, the C-ring 152 will expand and will fit on the outer periphery in the groove 157a. When the C-ring 152 thus fits in the groove 157, the fiber scope 148 and reinforcing sheath 154 will be connected with each other.

In the case of removing the reinforcing sheath 154, when the insertable part 12 is attempted to be pulled out of the sheath 154, the C-ring 152 will be removed out of the groove 157 and the sheath 154 and fiber scope 148 will be removed.

By the way, in this embodiment, only the reinforcing sheath 154 has been illustrated and explained but the nonillustrated curving device fitted sheath, channel fitted sheath, side viewing device fitted sheath, fixed brush fitted sheath, rotary hone fitted sheath and grinding device fitted sheath are also provided in the sheath body with the connecting metal piece 151 described in this embodiment in place of the connecting part 28 described in the first embodiment and are fitted to the insertable part 12 the same as is mentioned above.

The other formations, operations and effects are the same as in the first embodiment.

FIGS. 33 to 37 show the seventh embodiment of the present invention.

In this embodiment, the sheath is connected at the tip with the fiber scope. By the way, the same component members as in the first embodiment shall bear the same reference numerals and shall not be explained here.

The endoscope system of this embodiment comprises a fiber scope 161, a reinforcing sheath 162, a side viewing device fitted sheath 163 and a nonillustrated curving device fitted sheath, channel fitted sheath, fixed brush fitted sheath, rotary hone fitted sheath and grinding device fitted sheath.

The insertable part 12 of the above mentioned fiber scope 161 is provided at the tip with a tip body 164 formed of a small diameter part 166 and large diameter part 167 from the tip side. A male screw 168 is formed on the large diameter part 167. The small diameter part 166 is partly incised on the outer peripheral surface to form a plane part 165.

On the other hand, as shown in FIG. 35, the above mentioned reinforcing sheath 162 is provided at the tip of the sheath body 27 with a cylindrical mouthpiece 170 on the inner peripheral surface of which a female screw 175 is formed to be screwed with the male screw 168 of the above mentioned insertable part 12. Within the mouthpiece 170, a fixed metal piece 169 is rotatably engaged by a flange 169a provided on it, is formed to be substantially like a cylinder of an outside diameter somewhat larger than of the above mentioned small diameter part 166 and has a step 169b formed on the inner peripheral surface so that, in case the sheath 162 is screwed with the insertable part 12, the tip body 164 will contact on the tip surface with this step 169b. Such engaging member 171 is provided as a key or pin, and is provided in the part corresponding to the plane part 165 of the fixed metal piece 169 so as to regulate the rotation of the fixed metal piece 169 with respect to the tip body 164.

In the side viewing device fitted sheath 163, a visual field direction changing adapter 172 is bonded and fixed to the above mentioned fixed metal piece 169, is provided with a visual field direction changing optical system 173 consisting of a prism or objective lens system so that the optical axis may coincide with that of the objective lens system 18 of the fiber scope 161 and is also provided with an illuminating light transmitting light guide 174 as curved by about 90 degrees so that the entrance end surface may coincide with the light distributing lens system 19 of the fiber scope 161.

By the way, the fixed metal piece 169 to which the adapter 172 is bonded has no step 169b formed on the inner peripheral surface so that, in the case of screwing the sheath 162 with the insertable part 12, the adapter 172 will contact on the operating part 13 side end surface directly with the tip surface of the tip body 164. Also, the engaging member 171 performs the duty as of a positioning member for making the optical axes of the optical system of the fiber scope 161 and the optical system of the adapter 172 coincide with each other.

The other formations of the side viewing device fitted sheath 163 are the same as of the reinforcing sheath 162.

The nonillustrated curving device fitted sheath, channel fitted sheath, fixed brush fitted sheath, rotary hone fitted sheath and grinding device fitted sheath are also provided with the connecting part described in this embodiment in place of the connecting part 28 described in the first embodiment.

In this embodiment, particularly, in case the side viewing device fitted sheath 163 is fitted to the fiber scope 161, as the scope side optical system is fixed in the position nearest to the sheath 163 side optical system, the optical axes of the sheath side and scope side can be prevented from being displaced from each other.

The other formations, operations and effects are the same as in the first embodiment.

Figure 38:
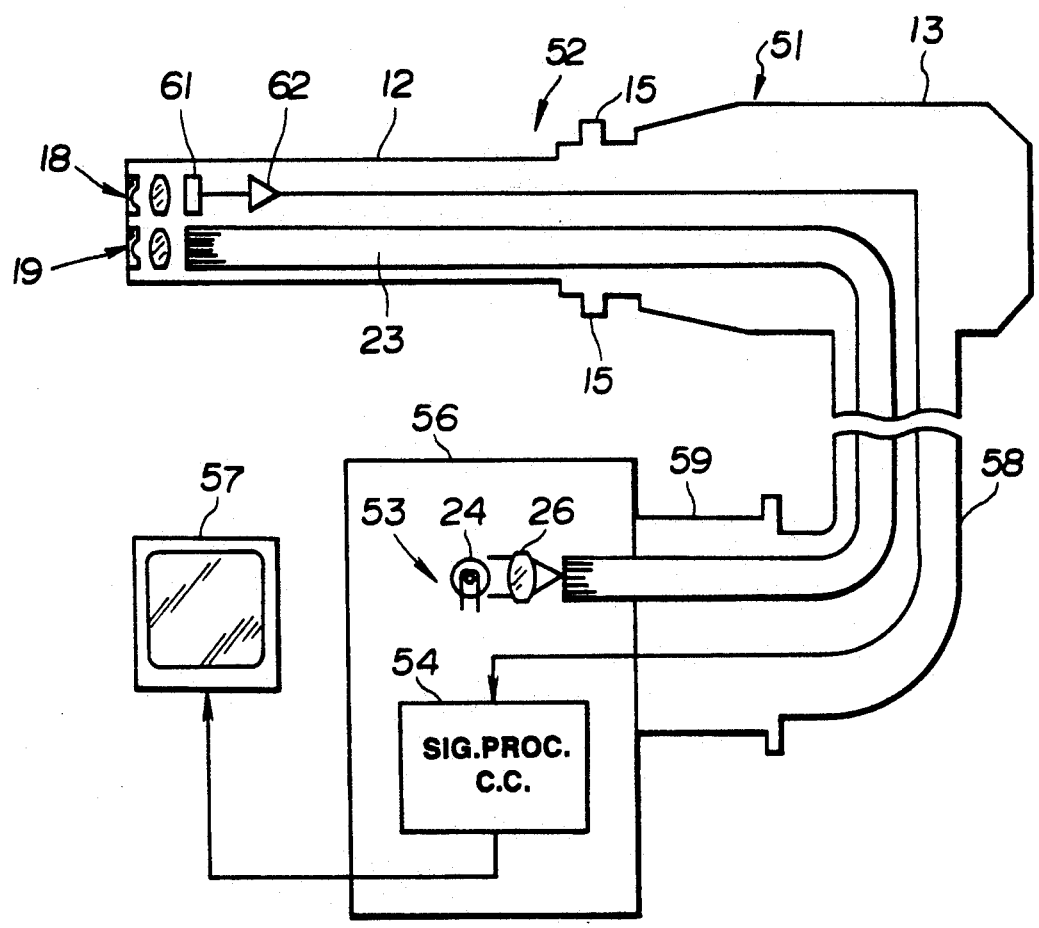

FIG. 38 shows the eighth embodiment of the present invention.

In this embodiment, an electronic endoscope is used in place of the fiber scope 2 described in the first embodiment and the other formations are the same as in the first embodiment.

The electronic endoscope apparatus 51 of this embodiment comprises an electronic endoscope 52, a control apparatus 56 having a light source part 53 and signal processing circuit 54 and a monitor 57 displaying an endoscope image.

The above mentioned electronic endoscope 52 has an insertable part 12 and an operating part 13 connected to this insertable at the rear end. A pin 15 for connecting the connecting parts 28 of the respective sheaths 4, 6, 7, 8, 9 and 11 described in the first embodiment is provided to project in the diametral direction at the front end of the operating part 13.

A universal cord 58 is extended out of the side of the above mentioned operating part 13 and is provided at the rear end with a connector 59 to be removably connected to the above mentioned control apparatus 56.

The insertable part 12 is provided at the tip with an objective lens system 18 as an observing window and a light distributing lens system 19 as an illuminating window. A solid state imaging device 61 is provided in the image forming position of the objective lens system 18 so that an object image taken in from the objective lens system 18 may be converted to an electric signal which is amplified by a pre-amplifier 62 and is delivered to a signal processing circuit 54 within the control apparatus 56 through the universal cord 58. The signal processing circuit 54 is connected to a monitor 57 so that a video signal produced in the signal processing circuit 54 may be transmitted to the monitor 57 and an endoscope image may be displayed on the picture of the monitor 57.

On the other hand, the exit end surface of the light guide 23 is arranged in the rear of the light distributing lens system 19 and this light guide 23 leads to the connector 59 through the operating part 13 and universal cord 58. When the connector 59 is connected to the control apparatus 56, an illuminating light emitted from the light source part 53 of the same formation as of the light source apparatus 3 described in the first embodiment will be radiated on the entrance end surface of the light guide 23.

The other operations and effects are the same as in the first embodiment.

As explained above, according to the present invention, as a plurality of sheaths different in the function and removably fitted to one endoscope are prepared, the sheaths selected as required can be combined with the endoscope and can be used for various uses.

In the above mentioned respective embodiments, the endoscope system formed of one fiber scope or electronic endoscope and a plurality of sheaths different in their functions and selectively connectable to this fiber scope or electronic endoscope, has been described. In the following, a light source connector for feeding the fiber scope or electronic endoscope with an illuminating light shall be described with reference to FIGS. 39 to 58.

Figure 39:
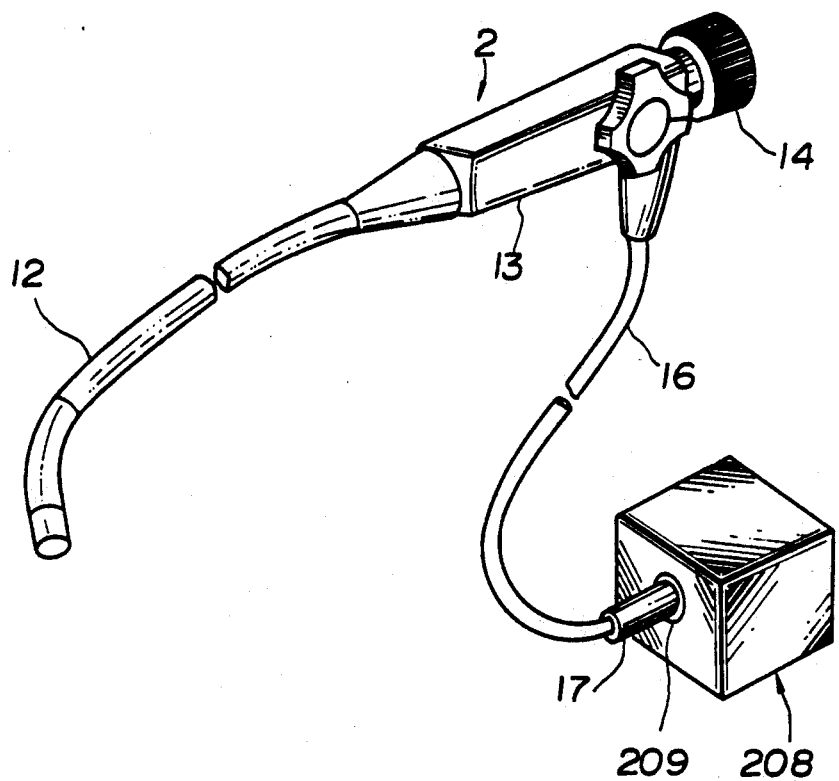

As shown in FIG. 39, the light guide hose 16 connected to the operating part 13 of the fiber scope 2 is provided at the end with a light source connector 17 which is removably connected to a light source apparatus 208 outputting an illuminating light.

The above mentioned light source apparatus 208 is provided with a receptacle 209 to which the above mentioned light source connector 17 is connected and at the rear end of which a light source —(—not illustrated—)— for feeding the illuminating light is provided.

The entrance end surface of the light guide leading the illuminating light is arranged in the connector 17 of the above mentioned fiber scope 2. This light guide is internally provided through the above mentioned light guide hose 16, operating part 13 and insertable part 12, has the exit end surface arranged on the tip surface of the above mentioned insertable part 12, leads the illuminating light fed to the entrance end surface and radiates it to the part to be inspected or the like from the exit end surface.

Figure 41:
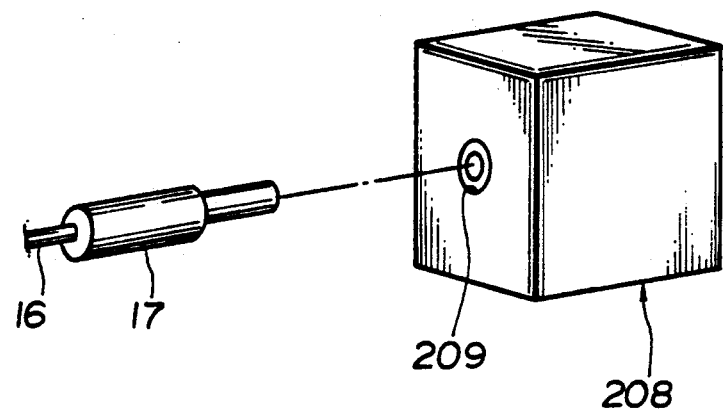

As shown in FIG. 41, when the above mentioned connector 17 is inserted into the above mentioned receptacle 209, the above mentioned fiber scope 2 and light source apparatus 208 will be removably connected with each other.

The connection of the above mentioned connector 17 and receptacle 209 with each other shall be explained with reference to FIG. 40.

Figure 40A:
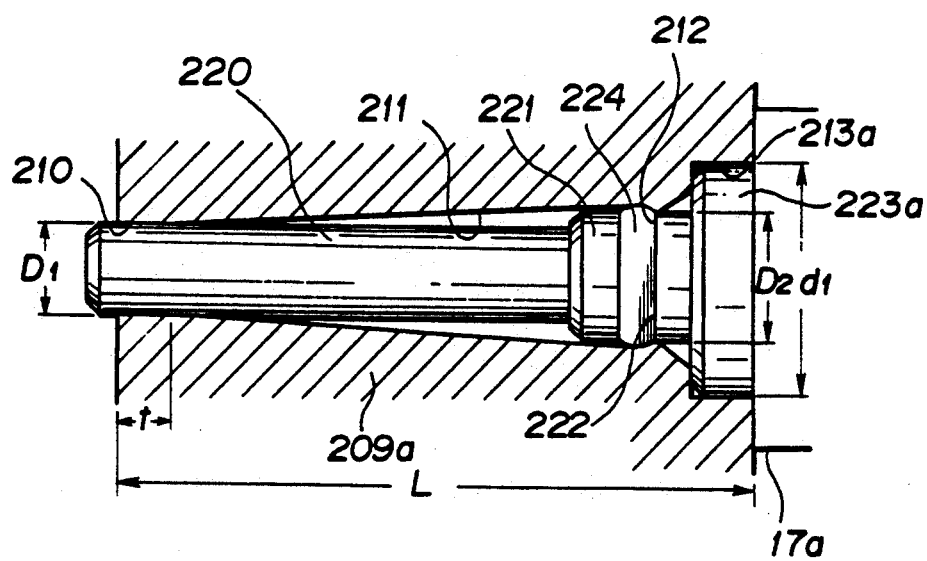
FIGS. 40(A)-40(C) are explanatory views relating to the connection of a connector and receptacle.
Figure 40B:
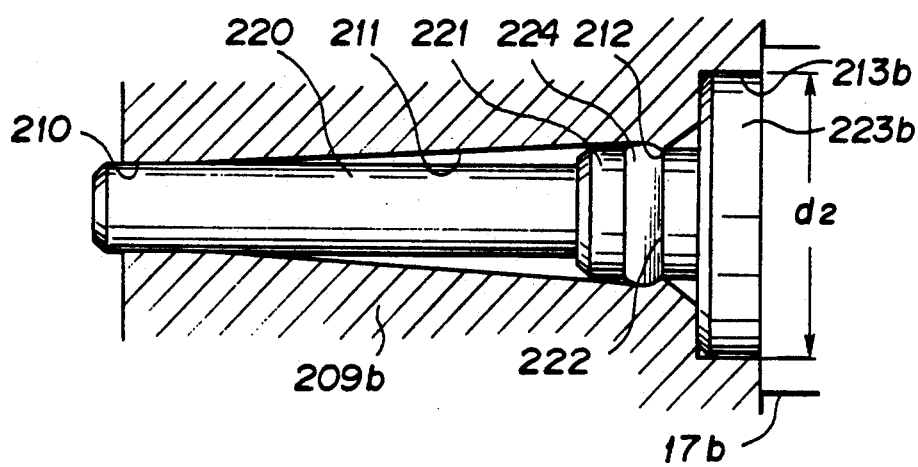
Figure 40C:
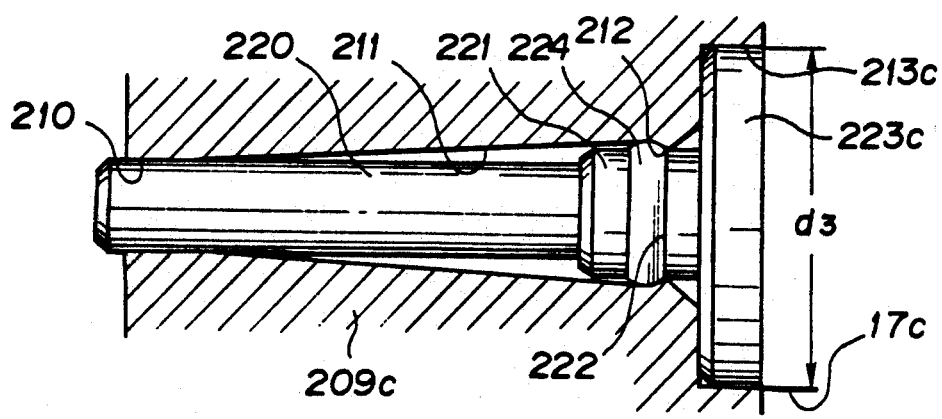

FIG. 40(A) is an explanatory view of the connection of a receptacle 209a of the light source apparatus 208 of a high luminance and high radiation heat using a xenon lamp for the above mentioned light source and a connector 17a internally provided with a light guide high in the heat durability against radiation heat with each other. FIG. 40(B) is an explanatory view of the connection of a receptacle 209b of the light source apparatus 208 of a medium luminance using a metal halide lamp for the above mentioned light source and a connector 17b internally provided with a light guide of a general heat durability against radiation heat with each other. FIG. 40(C) is an explanatory view of the connection of a receptacle 209c of the light source apparatus 208 of a low luminance using a halogen lamp for the above mentioned light source and a connector 17c internally provided with a light guide low in the heat durability against radiation heat with each other. By the way, the common explanation of the reference numerals 17a to 17c, 209a to 209c, 213a to 213c and 223a to 223c shall be made by omitting the signs of a to c.

The above mentioned connector 17 is provided with a substantially cylindrical insertable part 220 which is to be inserted and connected into the receptacle 209 provided in the light source apparatus 208. The above mentioned light guide is inserted through the above mentioned insertable part 220. Further, the entrance end surface of the above mentioned light guide is arranged on the tip surface of the above mentioned insertable part 220. The illuminating light by the above mentioned light source of the above mentioned light source apparatus 208 is fed to the entrance end surface of this light guide.

Figure 42:

The above mentioned insertable part 220 has a large diameter part 221 larger in diameter than the tip part and formed on the base end side to increase the strength on the base end side of the insertable part 220. This large diameter part 221 is provided peripherally with a groove 222 in which a C-ring 224 shown in FIG. 42 is to be fitted. When this C-ring 224 is fitted in the above mentioned groove 222 of the above mentioned large diameter part 221, the diameter of the C-ring can be made larger and the removably fitting force of the above mentioned insertable part 220 will be stabilized. A later described discriminating part 223 having heat durability, for example, against the radiation heat of the light guide inserted through the connector 17, is connected to the above mentioned large diameter part 221.

In the above mentioned receptacle 29, an inserting hole 211 through which the above mentioned insertable 220 is to be inserted is formed to be somewhat smaller in the lengthwise direction toward the tip. A supporting part 210 of an inside diameter somewhat larger than the outside diameter of the tip of the above mentioned insertable part 220 is formed on the tip side of the inserting hole 211. A projection 212 is peripherally formed on the base end side of this inserting hole 211 and in the position opposed to the above mentioned large diameter part 221. The discriminating part 213 discriminating the heat durability, for example, against radiation heat of the above mentioned connector 17 is formed from the base side of the above mentioned projection 212 to the outside end surface of the receptacle 209, that is, to the surface of the above mentioned light source apparatus 208. The length t in the lengthwise direction of the above mentioned supporting part 210 is made, for example, 1 mm. so that, when the above mentioned insertable part 220 is supported on the extreme tip side, the insertable part 220 will be controlled as much as possible from slightly moving in the diametral direction on the tip end surface. Thereby the illuminating light of the above mentioned light source can enter the above mentioned light guide without loss.

The inside diameter of the above mentioned projection 212 always presses the slope toward the rear end of the C-ring 224 so that the discriminating part 223 of the above mentioned insertable part 220 may be always energized to be pressed against the discriminating part 213. Thereby the above mentioned insertable part 220 is prevented from slightly moving in the axial direction at the tip. By the way, in the case of connecting the above mentioned insertable part 220 to the receptacle 209, the above mentioned C-ring 224 will be provided in such position that, when the slope toward the tip of the C-ring 224 contacts the projection 212, the insertable part 220 will have been inserted at the tip through the above mentioned supporting part 210 to prevent the insertable part 220 from being slightly moved at the tip and wrenched when the C-ring 224 passes over the projection 212. Further, when the above mentioned projection 212 is made small, it will give a clicking sense to the operator.

The diameter $D_1$ of the above mentioned insertable part 220 is set, for example, at 9.5 mm., the length L in the lengthwise direction of the above mentioned receptacle is set, for example, at 50 mm. and the outside diameter $D_2$ of the above mentioned large diameter part 221 is set, for example, at 13 mm. When the outside diameter $D_2$ of the above mentioned large diameter part 221 is made 13 mm., even with such lamp (light source) of a large bright point as a halogen lamp or metal halide lamp, the above mentioned light guide will be able to efficiently guide the illuminating light in.

In case the inside diameter of the discriminating part 213a of the above mentioned receptacle 209a and the outside diameter of the discriminating part 223a of the connector 17a are represented by $d_1$, the inside diameter of the discriminating part 213b of the above mentioned receptacle 209b and the outside diameter of the discriminating part 223b of the connector 17b are represented by $d_2$ and the inside diameter of the discriminating part 213c of the above mentioned receptacle 209c and the outside diameter of the discriminating part 223c of the connector 17c are represented by $d_3$, the relation of $d_1$, $d_2$ and $d_3$ will be $d_1 < d_2 < d_3$.

Figure 43:
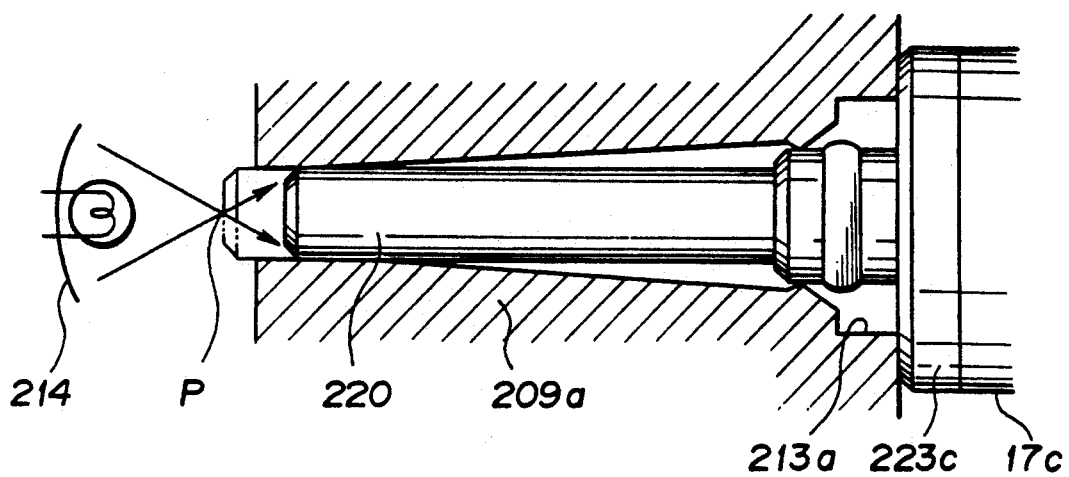

Therefore, in case the connector 17c internally provided with a light guide of a low heat durability is connected to the receptacle 209a of the light source apparatus 208 internally provided with the light source 214 of high radiation heat, as shown in FIG. 43, the above mentioned discriminating part 213a and the above mentioned discriminating part 223c will not engage with each other and the tip surface of the insertable part 220 of the above mentioned connector 17c will not reach the focus P of the illuminating light by the light source 214. Thereby, the illuminating light of the above mentioned light source 214 will be fed as made weaker than usual to the unit area of the tip surface of the above mentioned connector 17c, and the above mentioned light guide will be prevented from being burned by the infrared wavelength range of this illuminating light.

In other words, the above mentioned discriminating parts which are 213 and 223 display the other parts adapted to them.

Figure 44:
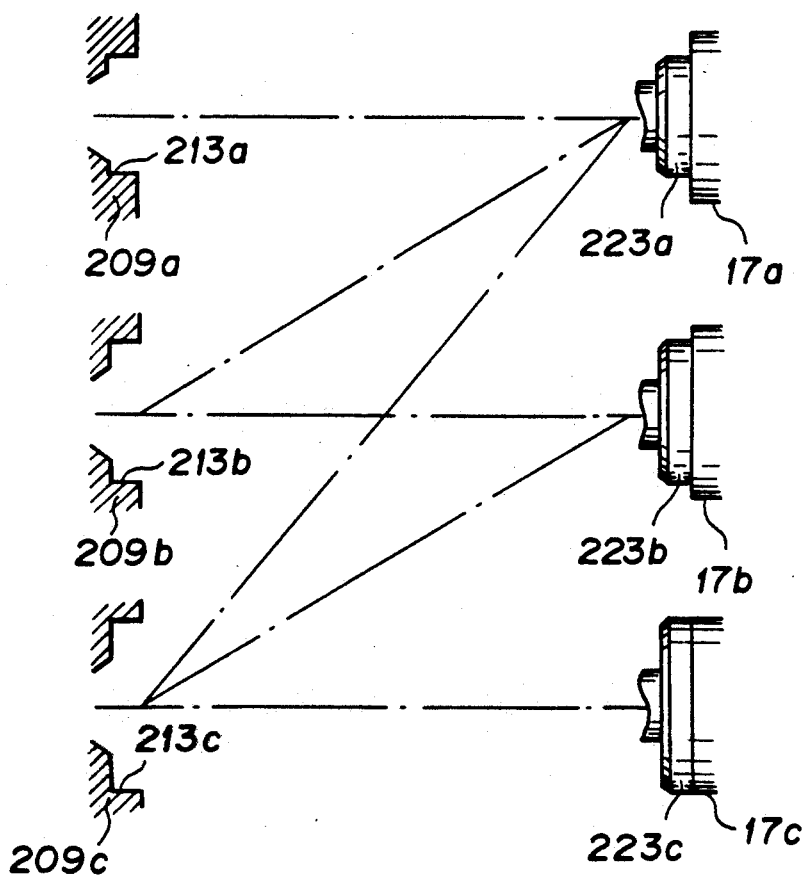

The connectability of the above described receptacles 209a to 209c and connectors 17a to 17c shall be explained with reference to FIG. 44.

The intensity of the radiation heat by the light source of the light source apparatus is represented by the reference numerals of the receptacles 209 to be 209a > 209b > 209c and the heat durability of the light guide inserted through the light source connector 17 is represented by the reference numerals of the connectors 17 to be 17a > 17b > 17c.

Therefore, the connector 17a is connectable to the receptacles 209a to 209c having the discriminating parts 213 of an inside diameter which can house the outside diameter of the discriminating part 223a, the connector 17b is connectable to the receptacles 209b and 209c having the discriminating parts 213 of an inside diameter which can house the outside diameter of the discriminating part 223b and the connector 17c is connectable only to the receptacle 209c having the discriminating part 213 of an inside diameter which can house the outside diameter of the discriminating part 223c.

That is to say, there is an effect that the connectability of the other part can be selected by the discriminating part 223 of the connector 17 and the discriminating part 213 of the receptacle 209.

By the way, the discriminating part 223 provided in the above mentioned connector 17 may be a discriminating part 223' formed of at least, for example, one pin as shown in FIG. 45. FIG. 45(A) shows the discriminating part 223' formed in the lengthwise direction of the above mentioned connector 17. FIG. 45(B) shows the discriminating part 223' formed vertically to the lengthwise direction of the above mentioned connector 17. Further, this discriminating part 223' is easy to form and the heat durability of the light guide internally provided in the light source plug 223 can be displayed to the operator by the number of the discriminating parts 223'.

Figure 46A:
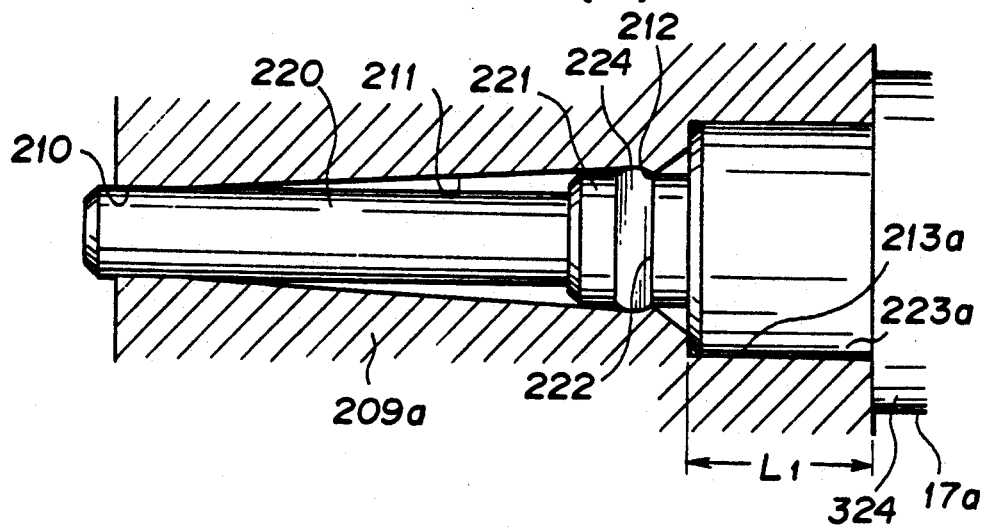
FIGS. 46(A)-46(C) are explanatory views relating to the connection of a connector and receptacle.
Figure 46B:
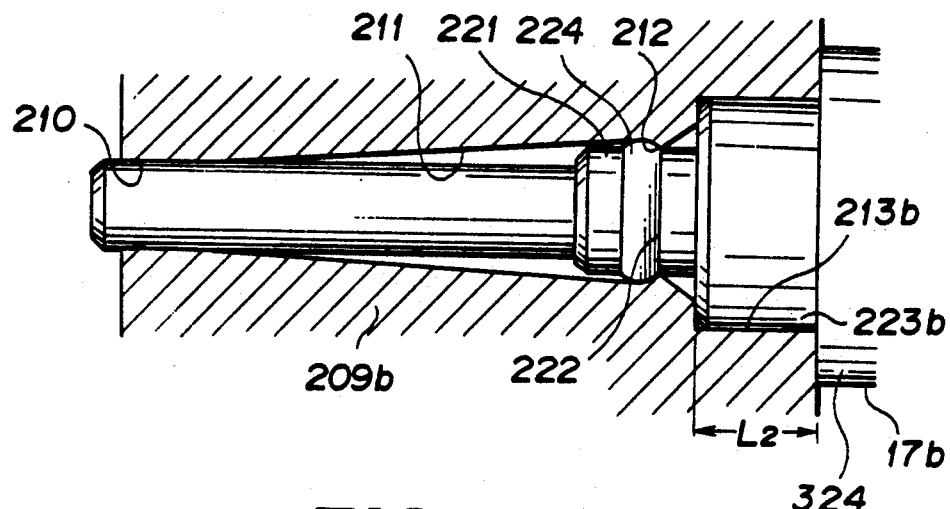
Figure 46C:
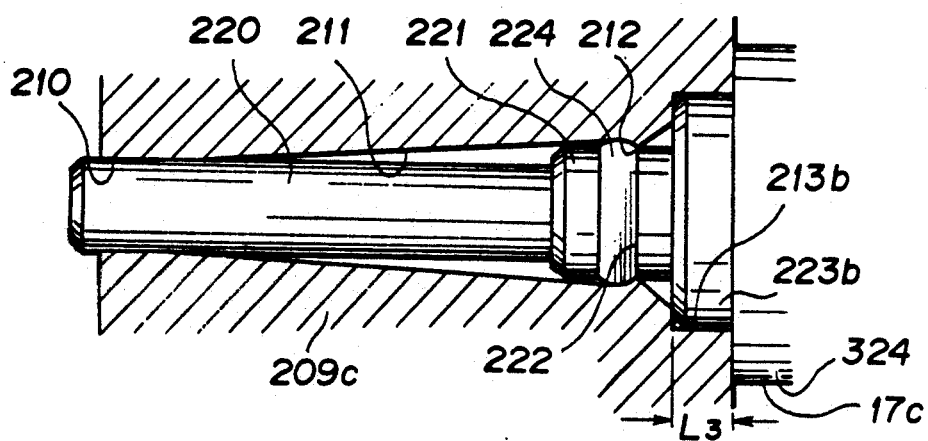

FIGS. 46 to 48 show other light source connectors 17. By the way, the same parts as in the above described FIGS. 39 to 45 shall bear the same reference numerals and shall not be explained here. In the common explanation of the reference numerals 17a to 17c, 209a to 209c, 213a to 213c and 223a to 223c, the reference signs a to c shall be omitted.

In the discriminating part 213 of the receptacle 209 in FIGS. 46 to 48, the length (depth) L in the lengthwise direction is different in response to the intensity, for example, of the radiation heat of the light source. Likewise, in the discriminating part 223 of the connector 17, the length L in the lengthwise direction is different in response, for example, to the heat durability of the light guide inserted through the connector 17. A regulating part 324 is provided at the rear end of this discriminating part 223. In case the length of the discriminating part 213a of the above mentioned receptacle 209a and the length of the discriminating part 223a of the connector 17a are represented by $L_1$, the length of the discriminating part 213b of the above mentioned receptacle 209b and the length of the discriminating part 223b of the connector 17b are represented by $L_2$ and the length of the discriminating part 213c of the above mentioned receptacle 209c and the length of the discriminating part 223c of the connector 17c are represented by $L_3$, the relation of $L_1$, $L_2$ and $L_3$ will be $L_1 > L_2 > L_3$.

Therefore, in case the connector 17c internally provided with a light guide of a low heat durability is connected to the receptacle 209a of the light source apparatus internally provided with a light source 214 of a high luminance and high radiation heat, as shown in FIG. 47, the regulating part 324 of the connector 17 will butt against the outer end surface 314 of the receptacle 209a and the tip surface of the insertable part 220 of the above mentioned connector 17c will not reach the focus P of the illuminating light by the light source 214. Thereby, the illuminating light of the above mentioned light source 214 will be fed as made weaker than usual to the unit area of the tip surface of the above mentioned connector 17c and the above mentioned light guide will be prevented from being burned by the infrared wavelength range of this illuminating light.

In other words, the above mentioned discriminating parts 213 and 223 display the other parts adapted to them.

That is to say, there is an effect that the connectability of the other part can be selected by the discriminating part 223 of the connector 17 and the discriminating part 213 of the receptacle 209.

By the way, the discriminating part 213 provided in the above mentioned receptacle 209 may be a discriminating part 213' formed, for example, of at least one pin as shown in FIG. 48. Further, this discriminating part 213' is easy to form.

Figure 49A:
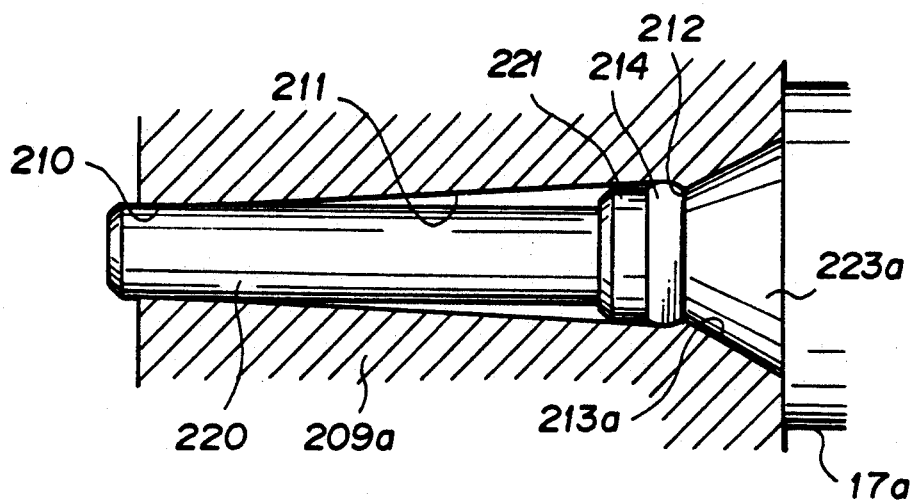
FIGS. 49(A)-49(C) are explanatory views relating to the connection of a connector and light source apparatus.
Figure 49B:
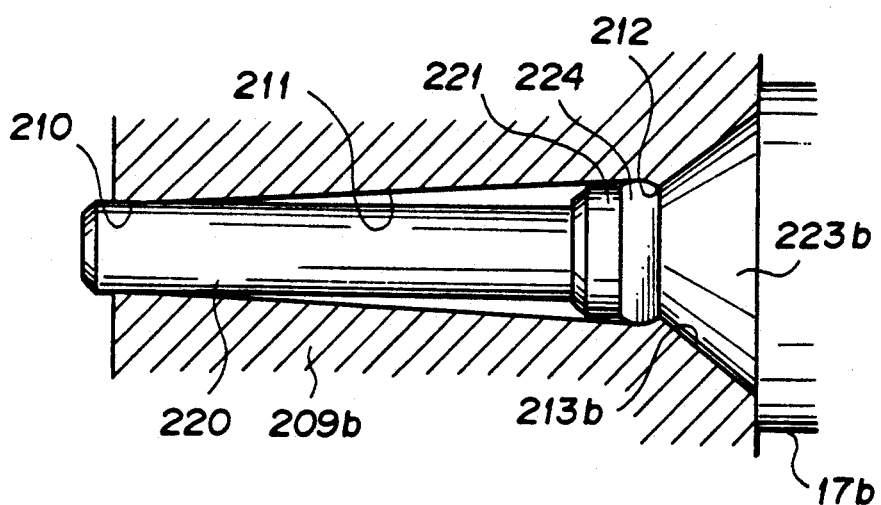
Figure 49C:
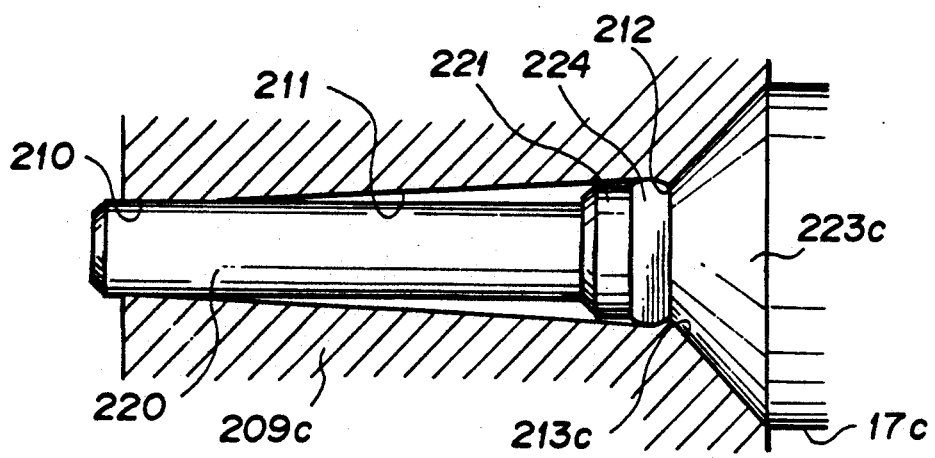

FIG. 49 is an explanatory view of the connection of a light source connector and receptacle with each other in a modification of the above mentioned light source connector 17.

In FIG. 49, the discriminating part 213 provided in the above mentioned receptacle 209 and the discriminating part 223 provided in the above mentioned connector 17 are formed to be tapered. This taper may be made to discriminate the other part by the taper angle or may be made in the same taper angle so that the other part may be discriminated by the length (depth) in the lengthwise direction.

Figure 50:
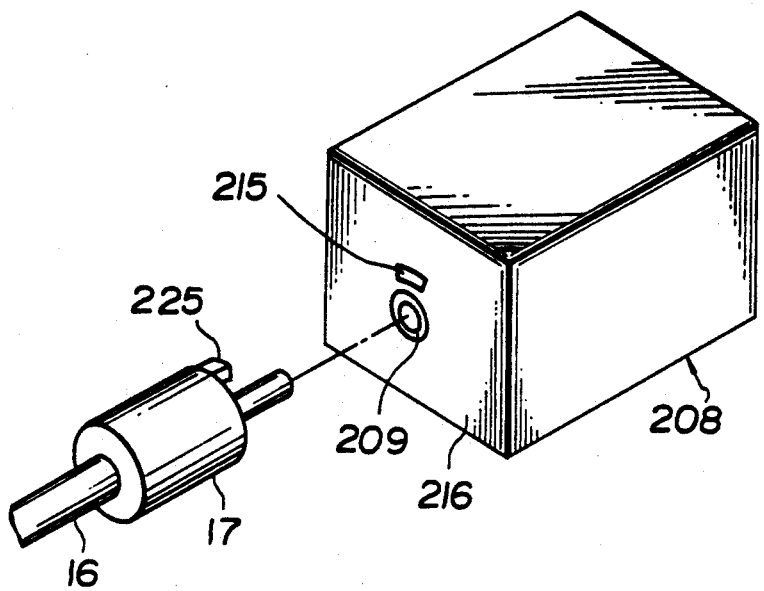
Figure 51:
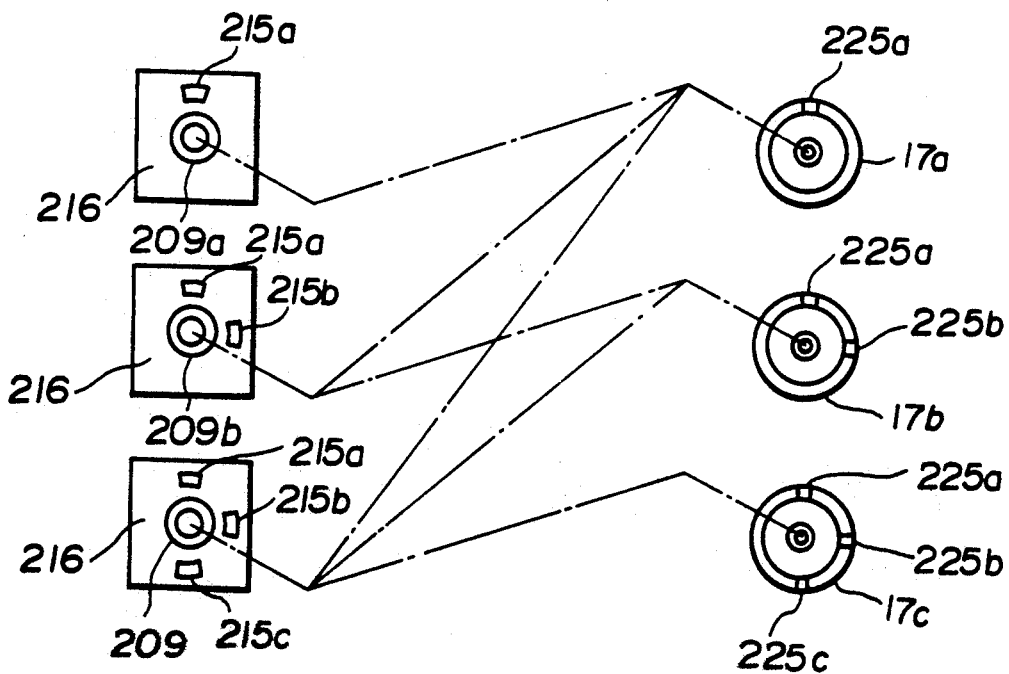

FIGS. 50 and 51 relate to other light source connectors. By the way, the same as in the above described FIGS. 39 to 45 shall bear the same reference numerals and shall not be explained here. In the common explanation of the reference numerals 17a to 17c, 209a to 209c, 215a to 215c and 225a to 225c, the signs a to c shall be omitted.

In the light source apparatus 208 in FIGS. 50 and 51, a discriminating recess 215 is formed near the receptacle 209 of the panel 216 provided with the receptacle 209. The light source connector 17 is provided with a discriminating projection 225, for example, by a pin. When this discriminating recess 215 and discriminating projection 225 engage with each other, the other part will be discriminated.

As shown in FIG. 51, the number of the discriminating recesses 215 will be different in response to the intensity, for example, of the radiation heat of the light source of the above mentioned light source apparatus 208 and the number of the discriminating projections 225 will be different in response, for example, to the heat durability of the light guide inserted through the above mentioned connector 17.

On the above mentioned panel 216, in case, for example, the radiation heat by the light source of the light source apparatus 208 is large, only the discriminating recess 215a will be provided, in case the radiation heat is normal, the discriminating recesses 215a and 215b will be provided and, in case the radiation heat is weak, the discriminating recesses 215a to 215c will be provided.

On the end surface opposed to the above mentioned panel 216 of the light source connector 17, in case, for example, the heat durability of the light guide inserted through the light source connector 17 is large, only the discriminating projection 225a will be provided, in case the heat durability is normal, the discriminating projections 225a and 225b will be provided and, in case the heat durability is weak, the discriminating projections 225a to 225c will be provided.

Therefore, in case the connector 17 weak in the heat durability is to be connected to the light source apparatus 208, for example, large in the radiation heat, any two of the above mentioned discriminating projections 225a to 225c will butt against the above mentioned panel 216 and no connection will be made. In case, the connector 17 large in the heat durability is to be connected to the light source apparatus 208 small in the radiation heat, the discriminating projection 225a will engage with any of the discriminating recesses 215a to 215c to connect them without any problem.

FIGS. 52 and 53 relate to other light source connectors 17. By the way, the same elements as in the above described FIGS. 39 to 45 shall bear the same reference numerals and shall not be explained here. In the common explanation of the reference numerals 17a to 17c, 209a to 209c, 215a to 215c and 225a to 225c, the signs a to c shall be omitted.

In the connector 17 in FIGS. 52 and 53, a rod lens 226 is arranged in the tip part and a light guide 227 is inserted in the rear of this rod lens 226. Further, the discriminating projections 225 explained in FIGS. 50 and 51 are peripherally formed on the outer periphery of the tip surface of the above mentioned connector 17.

Also, the discriminating recesses 215 explained in FIGS. 50 and 51 are formed on the outer surface or panel 216 of the above mentioned receptacle 209.

Therefore, in case the connector 17, which is low in heat durability, is to be connected, for example, to the light source apparatus which produces a relatively great amount of radiation heat, the above mentioned discriminating projections 225b and 225c will butt against the above mentioned panel 216 and no connection will be made. In case the connector 17 having a high heat durability is to be connected to the light source apparatus producing low radiation heat, the discriminating projection 225a will engage with the discriminating recess 215a to connect them without any problem. Also, there is no directionality for connecting the connector 17 to the receptacle 209, the connector 17 is rotatable with respect to the receptacle 209 and the light guide hose 16 is not stressed.

By the way, in FIGS. 50 to 53, the discriminating projection 225 may be provided in the connector 17 and the discriminating recess 215 may be provided in the receptacle 209.

Figure 54A:
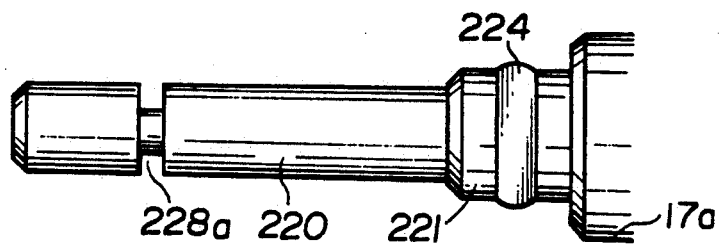
FIGS. 54(A)-54(D) are explanatory views of a connector.
Figure 54B:
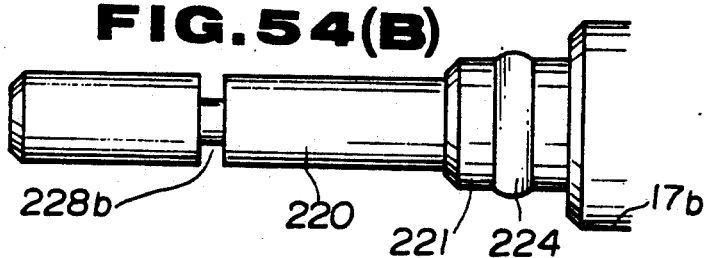
Figure 54C:
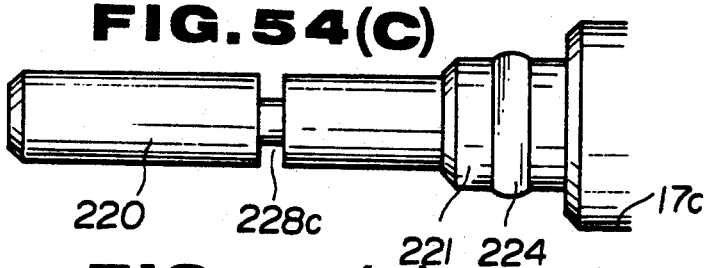
Figure 54D:
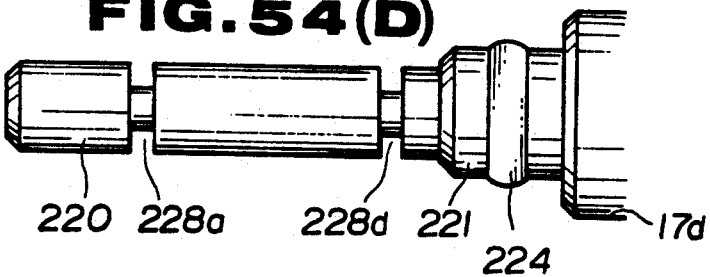
Figure 55:
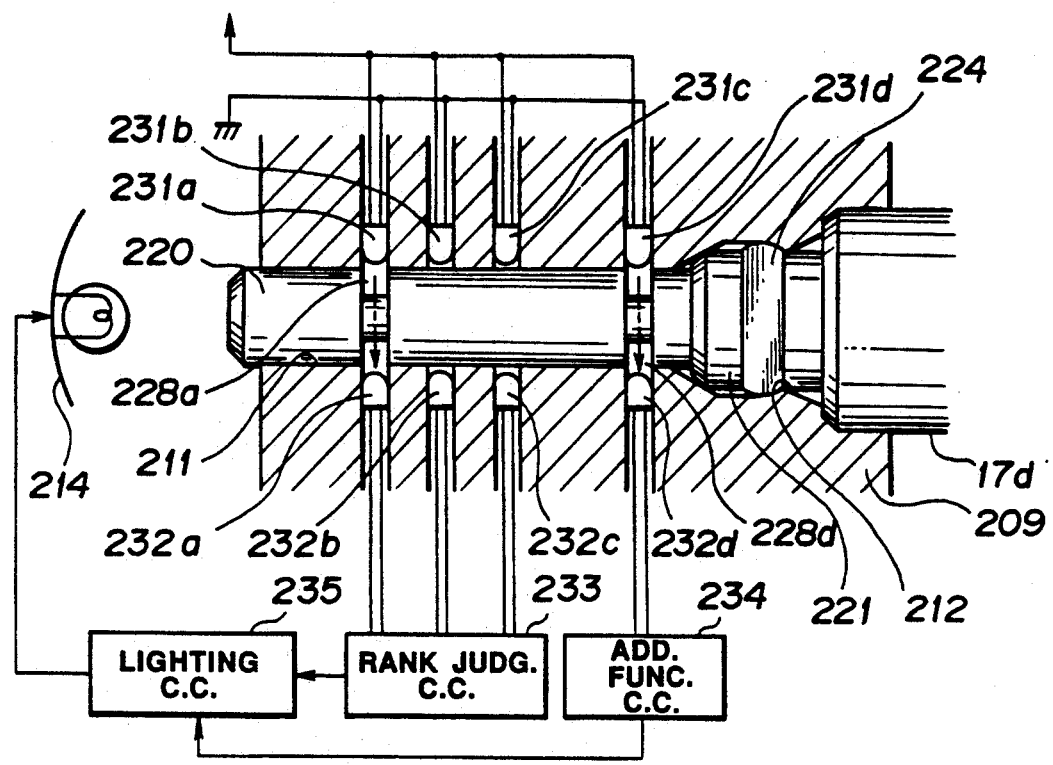

FIGS. 54 and 55 relate to other light source connectors 17. By the way, the same elements as in the above described FIGS. 34 to 45 shall bear the same reference numerals and shall not be explained here. In the common explanation of the reference numerals 17a to 17d and 228a to 228d, the signs a to d shall be omitted.

As shown in FIG. 54, a slit 228 made by reducing the outside diameter of the later described predetermined insertable part to be somewhat smaller, and representing the heat durability or the like of the light guide inserted through the connector 17, is formed in the insertable part 220 of the connector 17.

Also, in order to detect the above mentioned slit 228, light emitting devices 231a to 231d which are, for example, LED's and light receiving devices 232a to 232d which are, for example, phototransistors detecting the light from the above mentioned light emitting devices 231a to 231d, are provided together in the receptacle 209.

The above mentioned light emitting devices 231a to 231d are connected at one end to a driving power source and are grounded at the other end.

The above mentioned light receiving devices 232a to 232c are connected to a rank judging circuit 233 discriminating a rank which is a difference in the intensity of the heat durability of the light guide inserted, for example, through this connector 17. The above mentioned light receiving device 232d is connected to an additional function judging circuit 234 discriminating that, for example, even the same rank is a light source plug having an additional function of being able to increase the light amount.

The above mentioned rank judging circuit 233 is connected to a lighting circuit 235 connected to the above mentioned light source 214 and driving the light source 214 and controls, for example, the driving current of the above mentioned light source 214 by the above mentioned lighting circuit 235.

The above mentioned additional function judging circuit is also connected to the above mentioned lighting circuit 235 and further controls the driving current of the above mentioned light source 214.

As shown, for example, in FIG. 54(A), the light guide high in heat durability is inserted through the connector 17a in which the slit 228a is formed, as shown in FIG. 54(B), the light guide of a general heat durability is inserted through the connector 17b in which the slit 228b is formed, as shown in FIG. 54(C), the light guide low in heat durability is inserted through the connector 17c in which the slit 228c is formed and, as shown in FIG. 54(D), the light guide which can further increase the light amount in the light guide inserted through the light source connector 17 is inserted through the connector 17d in which the slits 228a and 228d are formed.

Therefore, for example, if the above mentioned connector 17d is inserted into the receptacle 209, as shown in FIG. 55, the lights of the light emitting devices 231a and 231d will pass the insertable part 220 through the slits 228a and 228d and will enter the light receiving devices 232a and 232d, but the lights of the light emitting devices 231b and 231c will be intercepted by the above mentioned insertable part 220 and will not enter the light receiving devices 232b and 232c.

Thereby, the rank judging circuit 233 controls the above mentioned lighting circuit 235 so as to be of the light amount corresponding to the above mentioned slit 228a. Also, the above mentioned additional function judging circuit 234 controls the above mentioned lighting circuit 235 to further increase the light amount controlled by the above mentioned rank judging circuit 233.

The above mentioned lighting circuit 235 feeds the light source 214 with a driving power by the control of the rank judging circuit 233 and additional function judging circuit 234 as described above, and this light source 214 feeds the light guide with an illuminating light of a light amount adapted to the light guide of the above mentioned connector 17d.

By the way, in order to eliminate the step difference of the insertable part 220 and to improve the insertability, for example, a black rubber member, which is a member low in light reflection factor, may be fitted to the slit so as to discriminate the rank with the light reflection factor.

Also, from the first, all the slits may be formed in the insertable part 220, such member transmitting no light as, for example, a carbon resin ring which may be fitted to the slit, and the light source connector may be made under the same standard as a rank corresponding to the light guide inserted through the light source connector.

Further, in case all the above mentioned light receiving devices 232a to 232d receive lights, the above mentioned connector 17 may be judged to have been pulled out and the driving power to the above mentioned light source 214 by the above mentioned lighting circuit 235 may be interrupted.

That is to say, there is an effect that various light source connectors can be formed by only forming the slits 228a to 228d adapted to the light source connectors without transforming the other members.

Figure 56:
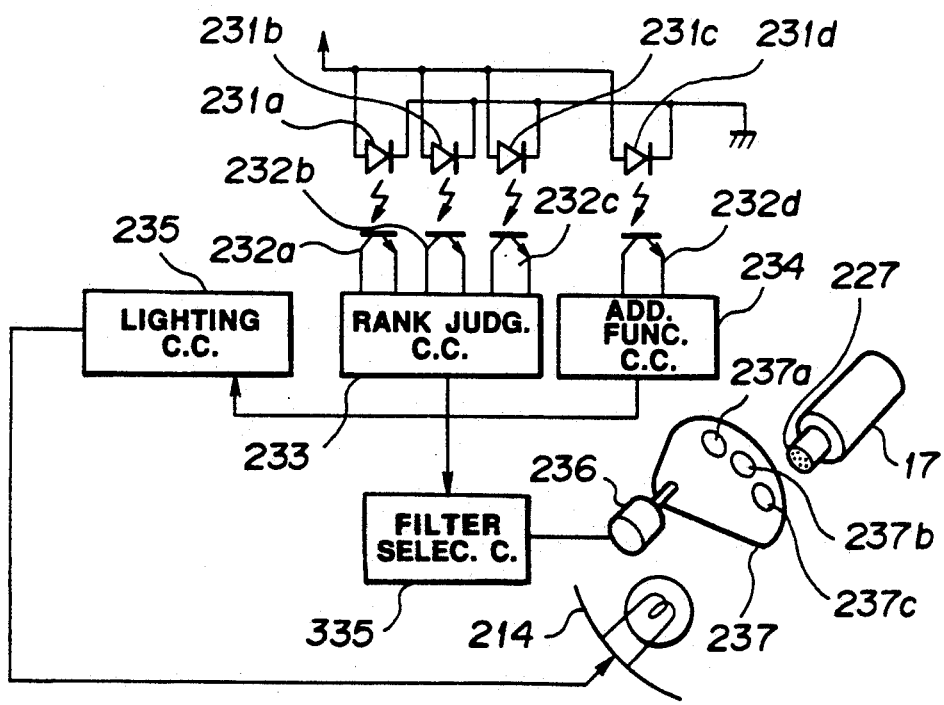

FIG. 56 relates to another light source connector 17. By the way, the same elements as in the above described FIGS. 39 to 45 shall bear the same reference numerals and shall not be explained here.

The receptacle and the light source connector inserted into the receptacle in FIG. 56 are the same as in FIGS. 54 and 55.

In FIG. 56, a rank judging circuit 233 is connected to a filter selecting circuit 335 selecting a filter by a servomotor so as to control the filter selecting circuit 335.

Also, an additional function judging circuit 234 controls, for example, the driving current of a light source 214 of a lighting circuit 235.

A servomotor 236 is connected to the above mentioned filter selecting circuit 335 and a filter plate 237 in which a plurality of filters 237a to 237c are arranged, is borne on the driving shaft of this servomotor 236.

The above mentioned filters 237a to 237c are respectively different, for example, in light transmittivity.

The above mentioned filters 237a to 237c are to be interposed in the light path of a light guide 227 inserted through the above mentioned light source 214 and connector 17 so as, for example, to increase or decrease the illuminating light by the above mentioned light source 214.

The above mentioned rank judging circuit 233 discriminates the rank of the connector from the inserted light source connector and outputs the signal of the result of this discrimination to the filter selecting circuit 335.

The above mentioned filter selecting circuit 335 drives the servomotor 236 by the signal of the result of the above described discrimination so that one of the filters 237a to 237c may be selected and may be interposed in the light path of the light guide 227 inserted through the connector 217, and the illuminating light of the light amount adapted to the light guide of the inserted light source connector may be fed to the light guide as described above.

By the way, in FIGS. 55 and 56, the rank judgment may be represented, for example, by a binary (BCD) code and 16 kinds may be discriminated in four slits.

Figure 57:
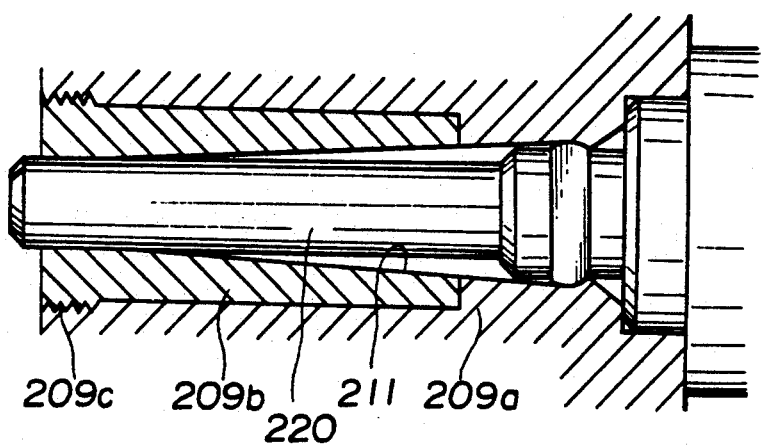

As shown, for example, in FIG. 57, the inserting hole 211 passed through the above mentioned insertable part 220 may be made by integrally screwing a member 209b, formed in advance to be somewhat smaller in the diameter in the lengthwise direction toward the tip, into a receptacle body 209a with a screwing part 209c by a male screw formed on the member 209b and by a female screw formed in the receptacle body 209a.

Also, the member 209b may be formed of such material softer than of the light source connector as, for example, a fluorine resin or polyamide resin to improve the connector 17 inserting feel.

Figure 58:
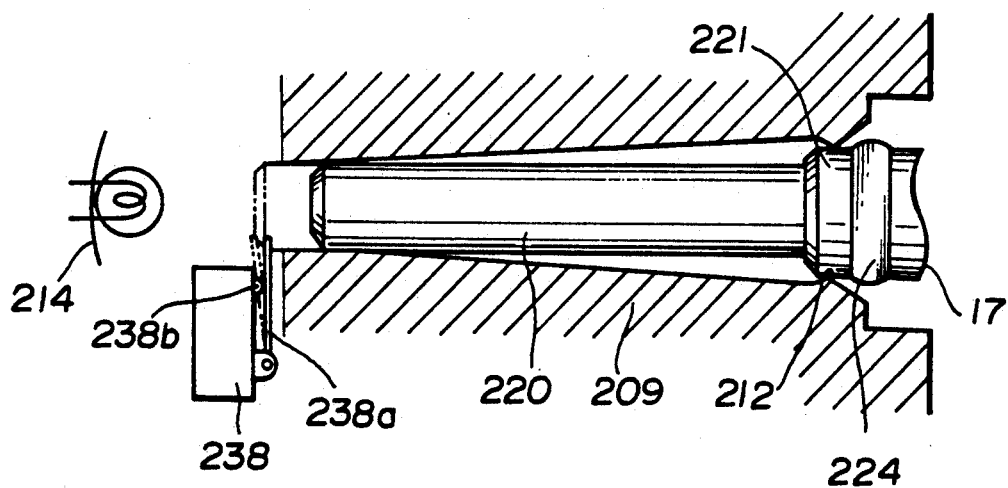

Also, for example, as in FIG. 58, a microswitch 238 may be provided to light the above mentioned light source 214 when the above mentioned connector 17 is inserted into the above mentioned receptacle 209, the above mentioned large diameter part 221 passes the above mentioned projection 212 and the above mentioned C-ring 224 passes over the above mentioned projection 212, that is, when the insertable part 220 projects out of the receptacle 209. In this microswitch 238, a lever 338 may be supported so as to contact, for example, the tip surface of the above mentioned projected insertable part 220 and may be arranged to be pushed by the above mentioned insertable part 220 to push the switch part 239b of the above mentioned microswitch 238 so that, when this switch part 238b is pushed, the light source 214 may be lighted.

By such formation as in FIGS. 39 to 58, the light source connector and receptacle can be standardized and the interchangeability can be elevated and, by discriminating the connectability of the opposed device, damage to the devices such as the burning of may be caused by light guide, can be prevented.

What is claimed is:

1. An endoscope system comprising:
    an endoscope having a tip part, said tip part including an insertable part which has an illuminating window for emitting light for illuminating an object and a receiving window for receiving an image of the object illuminated by said illuminating light emitted from said illuminating window; and
    a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions; each of said plurality of sheaths including connecting means for connection with said endoscope;
    wherein each of said connecting means is formed on an intermediate part of a respective one of said plurality of sheaths between the tip part and a base end part thereof, each of said sheaths being elongate and tubular and having on one end thereof a tip part to be inserted into an object to be inspected and a base end part positioned at said insertable part of said endoscope.

2. An endoscope system according to claim 1 wherein each of said connecting means is formed of a groove provided on the inner peripheral surface of said sheath to fit a spring member provided on the outer peripheral surface of said insertable part.

3. An endoscope system comprising:
    an endoscope having a tip part, said tip part including an insertable part which has an illuminating window for emitting light for illuminating an object and a receiving window for receiving an image of the object illuminated by said illuminating light emitted from said illuminating window; and
    a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions; each of said plurality of sheaths including connecting means for connection with said endoscope;
    wherein each of said connecting means is formed on a rear end of a respective one of said plurality of sheaths, each of said plurality of sheaths being elongate and tubular and having on one end thereof a tip part to be inserted into an object to be inspected and a base end part positioned at said insertable part of said endoscope.

4. An endoscope system according to claim 3 wherein each of said connecting means is formed of a screw part screwing with a screw part provided in said insertable part.

5. An endoscope system comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions; said plurality of sheaths having at least two of a reinforcing sheath, a channel fitted sheath, a visual field changing sheath, a manually operable sheath, and an electrically operable sheath;

wherein each of said plurality of sheaths includes a base end and a tip end, and wherein each of said plurality of sheaths includes a flexible portion at said tip end having curving means for causing curving of said flexible portion, and further comprising a controlling means for controlling curving of said flexible portion.

6. An endoscope system, comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions;

wherein each of said plurality of sheaths respectively includes a channel portion for receiving said insertable part therein and includes a treating instrument channel disposed along said inserting channel.

7. An endoscope system, comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions;

wherein one of said plurality of sheaths comprises a fixed brush fitted sheath having a brush disposed in a tip part of said sheath.

8. An endoscope system, comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions;

wherein one of said plurality of sheaths comprises a grinding device fitted sheath having a jetting port for ejecting a jet of grinding material, said jetting port being disposed in a tip part of said sheath.

9. An endoscope system, comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions;

wherein one of said plurality of sheaths comprises a sensor sheath removably fitted with a sensor adapter having a sensor.

10. An endoscope system, comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions, said plurality of sheaths having at least two of a reinforcing sheath, a channel fitted sheath, a visual field changing sheath, a manually operable sheath, and an electrically operable sheath;

wherein said endoscope includes a solid state imaging device for converting to an electric signal the object image taken in from said receiving window.

11. An endoscope system according to any of claims 6, 7, 8, 9, or 10, wherein each of said plurality of sheaths respectively includes a connecting means for the connection of a respective one of said plurality of sheaths with said endoscope.

12. An endoscope system according to claim 9 wherein said sensor sheath is connected to a sensor monitor for displaying the information detected by said sensor.

13. An endoscope system according to claim 12 wherein said sensor monitor has an eyepiece part for observing an object image of said endoscope so that the information together with the object image is observed.

14. An endoscope system, comprising:

an endoscope having a tip part, said tip part including an insertable part which has an illuminating window for emitting light for illuminating an object and a receiving window for receiving an image of the object illuminated by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions;

wherein one of said plurality of sheaths comprises a rotary hone fitted sheath having a rotary hone.

15. An endoscope system comprising:

an endoscope having a tip part, said tip part including an insertable part which has an illuminating window for emitting light for illuminating an object and a receiving window for receiving an image of the object illuminating by said illuminating light emitted from said illuminating window; and a plurality of sheaths selectively and removably connectable to said endoscope, each of said plurality of sheaths having a hollow interior portion for receiving said insertable part therein when connected to said endoscope, and said plurality of sheaths having respectively different structures for producing respectively different functions; said plurality of sheaths having at least two of a reinforcing sheath, a channel fitted sheath, a visual field changing sheath, a manually operable sheath, and an electrically operable sheath;

said plurality of sheaths each including respective connecting means for the connection of a respective one of said plurality of sheaths with said endoscope; and wherein said respective connecting means of each of said plurality of sheaths each has a substantially identical structure.

* * * * *